(12) United States Patent
Kiyota

(10) Patent No.: US 6,605,512 B2
(45) Date of Patent: Aug. 12, 2003

(54) MANUFACTURING METHOD OF A SEMICONDUCTOR DEVICE

(75) Inventor: Yukihiro Kiyota, Tachikawa (JP)

(73) Assignee: Hitachi, Ltd. (JP)

( * ) Notice: Subject to any disclaimer, the term of this patent is extended or adjusted under 35 U.S.C. 154(b) by 0 days.

(21) Appl. No.: 10/026,841

(22) Filed: Dec. 27, 2001

(65) Prior Publication Data

US 2002/0115228 A1 Aug. 22, 2002

(30) Foreign Application Priority Data

Feb. 21, 2001 (JP) ........................................ 2001-044910

(51) Int. Cl.[7] ............................................. H01L 21/336
(52) U.S. Cl. ......................................................... 438/296
(58) Field of Search ........................... 438/14, 15, 296; 324/158.1; 356/382

(56) References Cited

U.S. PATENT DOCUMENTS 5,465,154 A * 11/1995 Levy .............................. 356/382
5,719,495 A * 2/1998 Moslehi ....................... 324/158.1
6,387,764 B1 * 5/2002 Curtis ............................. 438/296

OTHER PUBLICATIONS

R.M.A. Azzam and N.M. Bashara, "Ellipsometry and Polarized Light", Chapter 5 "Instrumentation and Techniques of Ellipsometry", pp. 364–416.

A. R, Foroubi and I. Bloomer, "Optical Properties of Crystalline Semiconductors and Dielectrics", Physical Review B, vol. 38, No. 3 (Jul. 15, 1988), pp. 1865–1874.

* cited by examiner

Primary Examiner—John F. Niebling
Assistant Examiner—Andre C Stevenson

(57) ABSTRACT

The invention provides a non-destructive inspection method for a selectively grown film and a manufacturing method of a semiconductor device for providing a simple and convenient process control and throughput improvement. The method comprises forming a pattern in which selectively grown areas are closely arranged on a wafer for manufacturing an LSI, determining the film thickness and the composition of the selectively grown layer by analyzing optical constant data for the entire pattern, and feeding back the result to the next batch thereby conducting process control.

3 Claims, 22 Drawing Sheets

MANUFACTURING METHOD OF A SEMICONDUCTOR DEVICE

BACKGROUND OF THE INVENTION

1. Field of the Invention

This invention concerns a manufacturing method of a semiconductor device. In particular, the invention relates to analyzing optical constants of a measurement pattern on the semiconductor device thereby feeding back film thickness and composition data for adjusting the relevant manufacturing process.

2. Description of Related Art

As a method for measuring the composition and the thickness of a thin film used in a semiconductor, ellipsometry, has been generally adopted. FIG. 11 shows an example of an ellipsometric device, a spectro-ellipsometer, which measures light-polarization rotation.

An incident light emitted from a light source 20 is passed through a modulator 21 and separated by a polarizer 22 into a P-polarized component and an S-polarized component. The incident light is reflected by an object of interest 23, passed through a detector 24 and then polarized by a polarizer 25 into lights at wavelength from 250 nm to 830 nm. The spectralized light at each wavelength is adapted to be detected by a detector 26.

This method is adapted to enter a P-polarized light and an S-polarized light into a sample and determine the film thickness or the like based on the amplitude and the phase difference of the reflected lights, which is used generally as a method for measuring a thin film grown on the entire surface of a semiconductor wafer. In this case, the ellipsometric angle ($\phi$, $\Delta$) is defined through a complex reflection coefficient ratio p (ratio of the reflection coefficient rp of the P-polarized light, and the reflection coefficient rs of the S-polarized light) by the following equation:

$$\rho = rp/rs = \tan\phi \cdot \exp(j\Delta)$$

$$\tan\phi = |rp|/|rs|$$

$$\Delta = \delta RP - \delta RS$$

That is, $\tan\phi$ represents a difference of amplitude, and $\Delta$ represents a constant indicating a phase difference between P-polarized light and S-polarized light. The film thickness, the composition or the like of the sample of interest can be determined by determining $\phi$ and $\Delta$ of the sample by comparing them with those of a known substance.

Usually, the spot size of incident light is several mm, which can be restricted to several tens $\mu$m. However, the restriction of the incident light involves a problem that the signal intensity is decreased and the measuring accuracy is reduced. The incident angle and the reflection angle are usually about from 50° to 75°. This technique is described in "ELLIPSOMETRY AND POLARIZED LIGHT", R. M. A, AZZAM AND N. M. BASHARA, NORTH-HOLLAND PUBLISHING COMPANY, 1977, pp 364–416.

Another method for measuring the thin film used on a semiconductor wafer is a reflectance method, and FIG. 12 shows the device and the principle thereof. In this technique, a white light at a wavelength, for example, of 200 nm to 900 nm is emitted from a light source 20 and entered at an angle nearly vertical to the sample 23, and the reflectance R of the light is measured by a detector 26. The reflectance R is generally represented by the following equation:

$$R = ((n-1)^2 + k^2)/((n+1)^2 + k^2)$$

where n represents a refractive index and k represents an extinction coefficient.

This is a method for determining the film thickness and the composition of a substance based upon the principle that the wavelength dependence of n and K is a function of an energy gap of the substance. Since a perpendicular incident light is used in this method, the spot area on the sample is smaller compared with that in the ellipsometry, but it also has another problem that the restriction of the incident light decreases the signal intensity and the measuring accuracy. Further, it is difficult to apply an incident light to a fine pattern of 1 $\mu$m or less. This technique is described in "OPTICAL PROPERTIES OF CRYSTALLINE SEMI-CONDUCTORS AND DIELECTRICS" A. R. FOROUHI AND I. BLOOMER, PHYSICAL REVIEW B. 38, P. 1865, (1988).

The base area of an SiGe hetero bipolar transistor is formed by SiGe epitaxial growth in which a selective growth method of depositing only on a fine transistor pattern is used. A cross sectional view of a hetero bipolar transistor using selective growth is shown in FIG. 13.

After forming a stacked film comprising a first silicon oxide film 30, a silicon nitride film 31, a polysilicon layer 32 for extrinsic base, and a second silicon oxide film 33, a predetermined transistor pattern is etched to expose the surface of a silicon substrate 3. Then, an SiGe selectively grown layer 34 as the base area of the transistor is formed only to the area where silicon is exposed. In the selective growth described above, since a so-called loading effect is often caused that a grown film thickness differs depending on the size of the grown area, the thickness of the actual film grown on the transistor area is different from that grown on a large area.

FIG. 14 shows an example of a loading effect, from which it can be seen that the selective growth thickness differs greatly depending on the area of the window in the dielectric film. Further, even the growth rate is decreased by lowering the growth pressure from 10000 Pa to 1000 Pa, the loading effect can not be eliminated completely. Accordingly, the thickness of the film grown on the actual transistor area can not be known unless the thickness of the film grown on the pattern of the same area as that for the transistor area is measured.

The transistor area often forms in a rectangular shape, for example, of about 0.2 $\mu$m×4 $\mu$m, but it is difficult to transmit a light beam only to such a fine pattern by the ellipsometry described above. Accordingly, the film thickness of the selectively grown layer is confirmed by observing the cross section of a transistor main body under destructive inspection, such as by using a scanning type electron microscope.

The measurement of the film thickness on the fine pattern by the ellipsometry is extremely difficult since the signal intensity is low and tends to be interfered by the circumstantial structure. Further, the method for measuring the fine cross section of a transistor with a microscope requires much labor and is not usable in the product line since this applies destructive detection. That is, the thin film has been measured by using a sample wafer instead of the manufactured device wafer itself As described above, it has been difficult to measure the composition and the thickness of a fine selectively grown semiconductor thin film by a non-destructive test. However, in the mass producing LSIs, it is necessary to control the process quality with a non-destructive inspection method. That is, it has been required for a method for determining a thickness of a selectively grown layer with respect to a wafer main body used for manufacturing the device, instantly feeding back a failure, if occurs, to a next batch so as to re-design the growth conditions.

SUMMARY OF THE INVENTION

This invention has been accomplished in view of the foregoing and it intends to provide a non-destructive inspection method for a selectively grown film and provide a manufacturing method of a semiconductor device for attaining a simple and convenient process control and improvement of the throughput.

In accordance with this invention, for attaining the foregoing object, an area larger than the spot size of an incident light of an ellipsometer (ellipsometric device) in which fine transistors are present densely is provided on a wafer for preparing LSI, and the optical constants of the entire area are determined by ellipsometry. By the analysis of the result, the thickness of an SiGe film, for example, grown selectively on the fine transistor pattern is determined. The growing conditions for the next batch of the thin film are determined based on the result of the measurement. Such a technique is effective in a so-called batchwise processing device in which wafers are treated sheet by sheet.

As described above, this invention has a feature in determining the thickness and/or the composition of a thin film grown in at least one trench on a semiconductor wafer on which surface plural substances are exposed by using a measurement pattern formed on the semiconductor wafer thereby determining growth conditions for a next batch of the thin film based on the comparing result.

This invention also has a feature in the constitution described above in that the measurement pattern has a larger area than the spot size of an incident light of the ellipsometer, while optical constants over the entire area are determined byellipsometry. The thickness of the thin film is measured based on the thus determined result, and the growth conditions for a next batch of the thin film are decided based on the measuring result.

This invention further has a feature of using a measurement pattern disposed on a wafer for manufacturing a semiconductor device having a thin film formed on a semiconductor substrates in which plural substances are exposed on the surface thereof and in which an area ratio between an area containing plural substances exposed on the wafer surface and other area is already known, then measuring optical constants of the entire measurement pattern before and after the growth of the thin film by ellipsometry, and determining the thickness and the composition of the thin film grown on each of the plural substances based on the measuring result.

This invention has a further feature in the constitution as described above in that the differential spectrums of optical constants before and after the growth of the thin film are analyzed based on the area ratio of the plural substances being exposed on the wafer surface before the formation of the thin film and the thickness and the composition of the thin film are determined based on the analyzing result.

This invention has a further feature in the constitution described above in that the measurement pattern comprises a semiconductor integrated circuit itself and is disposed by at least one semiconductor integrated circuit pattern.

This invention further has a feature in comprising a step for forming a dielectric film on the surface of a semiconductor substrate, a step for forming a window in the dielectric film through which a portion of the surface of the semiconductor substrate is exposed, a step for growing a semiconductor in the window, and the steps of determining the dielectric film thickness using the semiconductor as a measurement pattern and deciding growth conditions of the film thickness for next batch based on the determining result.

Other and further objects, features and advantages of the invention will appear more fully from the following description.

BRIEF DESCRIPTION OF THE DRAWINGS

The preferred embodiments of the present invention are illustrated in the accompanying drawings in which.

DETAILED DESCRIPTION OF THE PREFERRED EMBODIMENTS

This invention is to be explained by way of the preferred embodiments with reference to the drawings.

Figure 1:
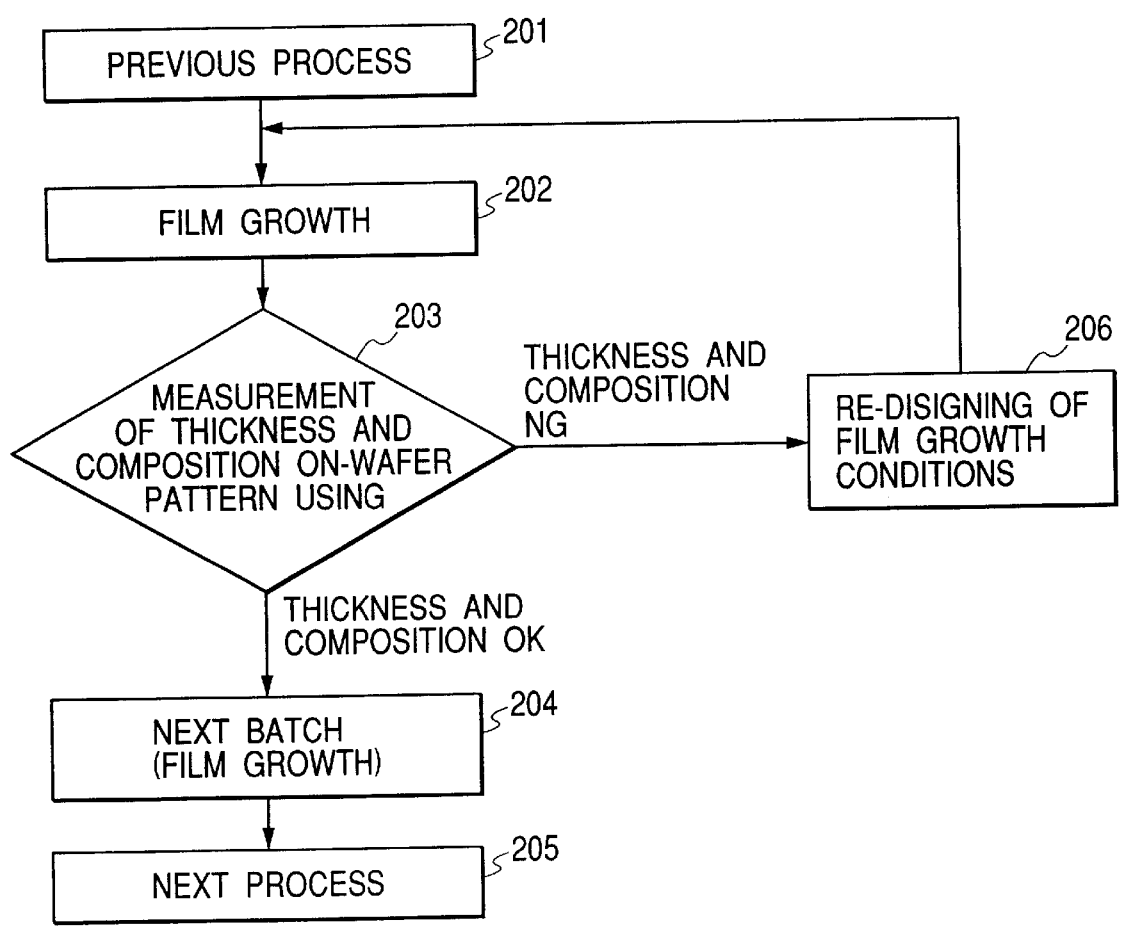
FIG. 1 is a flowchart of a manufacturing method of a semiconductor device as a first embodiment according to this invention.

FIG. 1 shows a manufacturing method of a semiconductor device as a first embodiment according to this invention. After a previous process (201) including, for example, thin film formation, photolithography and etching, a thin film is grown on a semiconductor wafer in which plural substances, for example, a single crystalline silicon layer and a dielectric film are present on the surface thereof (202). That is, a batchwise processing for thin film growth (a series of processes for processing a wafer in a reaction chamber of a thin film growing apparatus) are conducted. The batchwise processing includes not only processing for plural wafers but also batchwise processing. The thin film means herein, for example, single crystal silicon, polysilicon, mixed crystal of silicon and germanium, and tungsten.

The optical constants for the entire on-wafer measurement pattern formed in a semiconductor integrated circuit pattern are measured, for example, by ellipsometry after the growth of the thin film. The result is analyzed to determine, for example, the thickness and the composition of the thin film grown on the single crystal silicon (203). When the result is satisfactory (OK), thin films are grown under the same conditions in and after the next batch (204), and the process continues to the next process (205). If the result is different from the desired one (NG), the film growth conditions are re-designed (206), and the thin film is grown in the next batch under the redesigned conditions. By using this manufacturing method, the thin film growth process can be controlled precisely to decrease any variation of the film thickness between each of the wafers. Further, the "next batch" means herein the next batch of wafer processing after the wafer that has been monitored for the composition and the thickness of the thin film.

Figure 2:
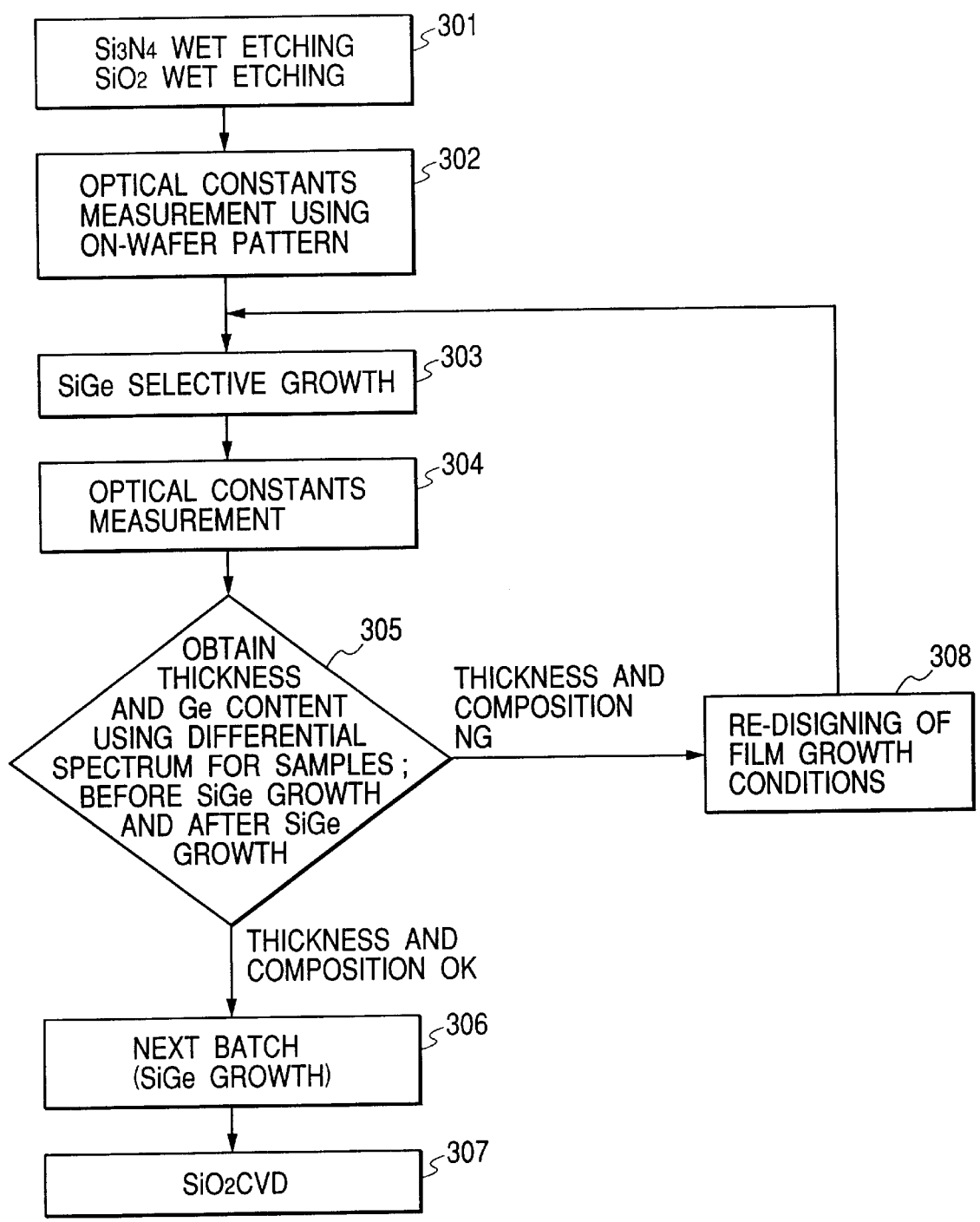
FIG. 2 is a flowchart of applying a manufacturing method of an SiGe hetero bipolar transistor as a second embodiment according to this invention.

FIG. 2 shows an example of applying a manufacturing method of a semiconductor device as a second embodiment according to this invention to manufacture a hetero bipolar transistor using SiGe. After the previous step (301) including thin film formation, photolithography and wet etching for $Si_3N_4$, $SiO_2$, the optical constants of the entire measurement pattern on the semiconductor wafer in which plural substances, for example, single crystal silicon and dielectric film are present on the surface are measured, for example, by ellipsometry (302).

Then, the mixed crystals of single crystal silicon and germanium are grown (303). After the thin film growth, optical constants for the entire measurement pattern formed in a semiconductor integrated circuit pattern are measured again (304). A differential optical spectrum before and after the thin film growth is extracted, and the result is analyzed to determine the optical constants only for the grown thin film and, further, the thickness and/or the composition of the growth thin film (305). If the result is satisfactory (OK), the thin film is grown under the same conditions for the next batch (306), and the process continues to the next process ($SiO_2CVD$) (307). If the result is different from the desired one (NG), the thin film growth conditions are redesigned (308), and the thin film in the next batch will be grown under the redesign conditions. The thickness and the composition of the grown thin film can be determined precisely according to this method.

Figure 3:
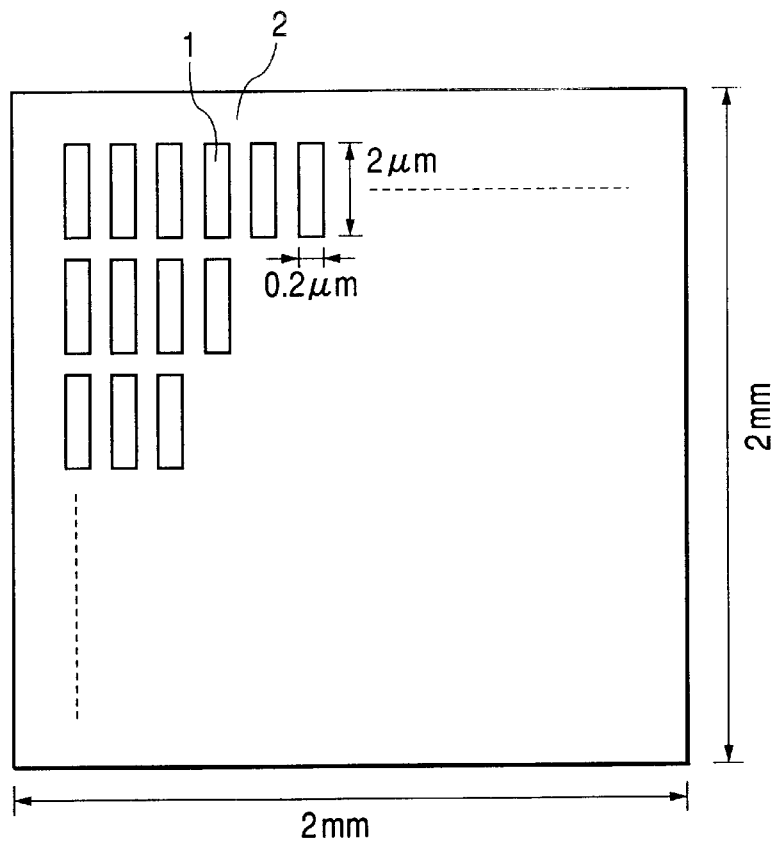
FIG. 3 shows a measurement pattern of a semiconductor wafer in a third embodiment according to this invention.

FIG. 3 is a plan view of a measurement pattern on a semiconductor wafer of a third embodiment according to this invention. In this embodiment, the area ratio between windows 1 for selective growth and the other area 2 is made substantially equal. The window 1 for selective growth has a rectangular shape of 0.2 µm×2 µm as an actual transistor where silicon substrate is exposed.

The window 1 for selective growth may be slitwise with 0.2 µm width. The area 2 (other than the window for selective growth) is covered with a silicon oxide film or a silicon nitride film. Further, the pattern size was 2 mm×2 mm, which is greater than the spot size of incident light, such that the incident light of the ellipsometer hits at only the inside of this pattern.

The area ratio between the window 1 for selective growth and the other area 2 may not be identical with each other as in this embodiment, as long as that the area ratio is previously known.

Figure 4:
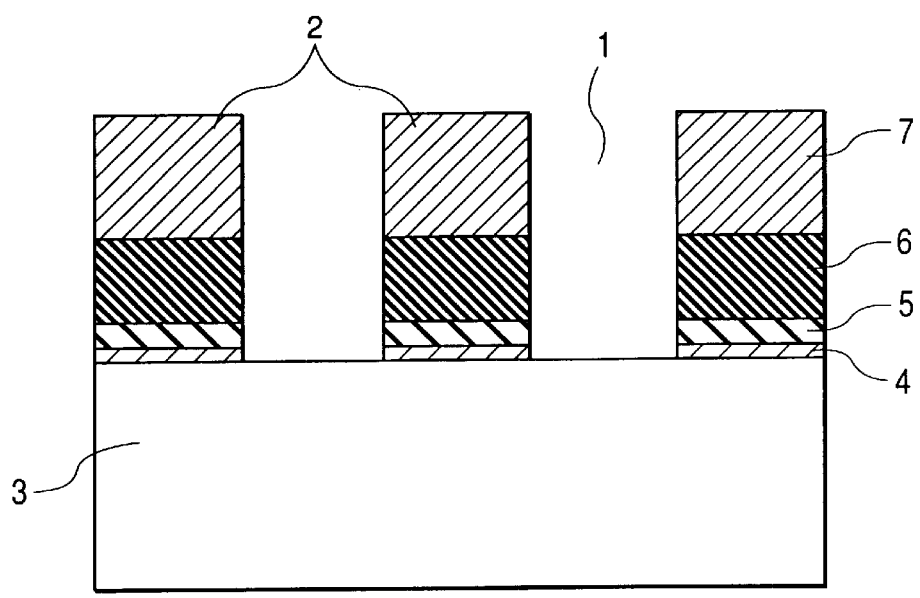
FIG. 4 is a cross sectional view of the measurement pattern shown in FIG. 3.

FIG. 4 is a cross sectional view of a measurement pattern of the third embodiment according to this invention. After stacking a silicon substrate 3, a first dielectric film 4, a second dielectric film 5, a polysilicon layer 6, and a third dielectric film 7, an exposed portion of silicon as the window 1 for selective growth is formed by photolithography and etching. The width for the silicon exposed portion as the window 1 is, for example, 0.2 µm. The area ratio between the window 1 for selective growth and other area 2 is 1:1.

Figure 5:
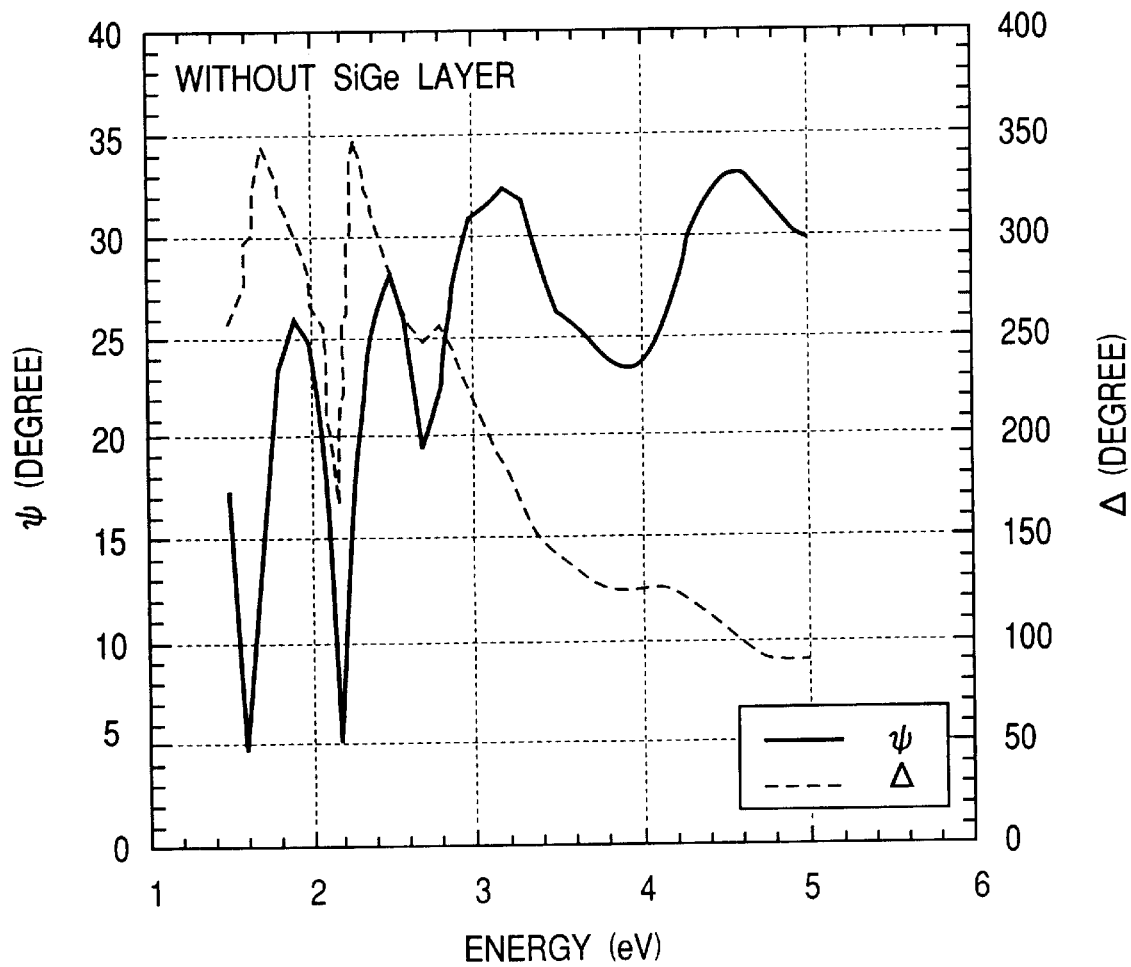
FIG. 5 shows the result of spectral ellipsometry before selective and epitaxial growth of SiGe showing the third embodiment according to this invention.

FIG. 5 shows a result of optical constants ($\phi$ and $\Delta$) measured by a spectral ellipsometer with white light before SiGe epitaxial growth on the pattern shown in FIG. 4. The results include the optical constants for the stacked film comprising the first dielectric film 4, the second dielectric film 5, the polycrystalline silicon layer 6, the third dielectric film 7, and the portion where the silicon substrate is disposed shown in FIG. 4. A similar result can also be obtained by analyzing other optical constants, such as dielectric constant ϵr and ϵI, or refractive index n and k, instead of ϕ, Δ.

Figure 6:
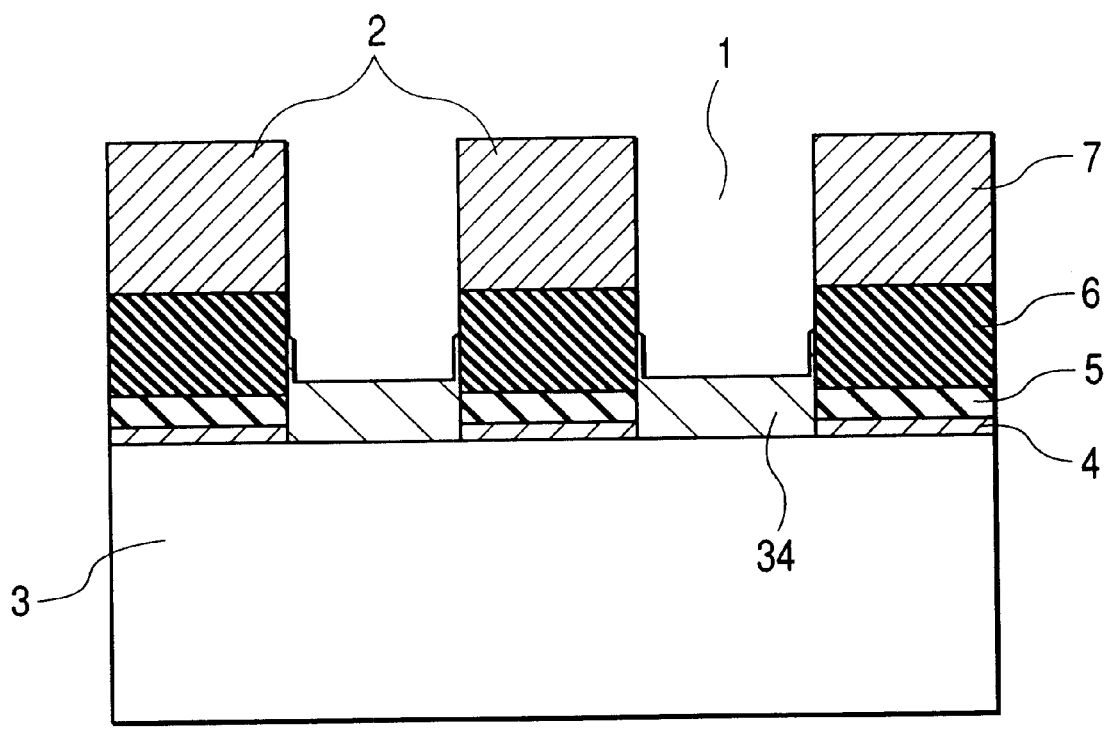
FIG. 6 is a cross sectional view after the selective epitaxial growth of SiGe showing the third embodiment according to this invention.
Figure 7:
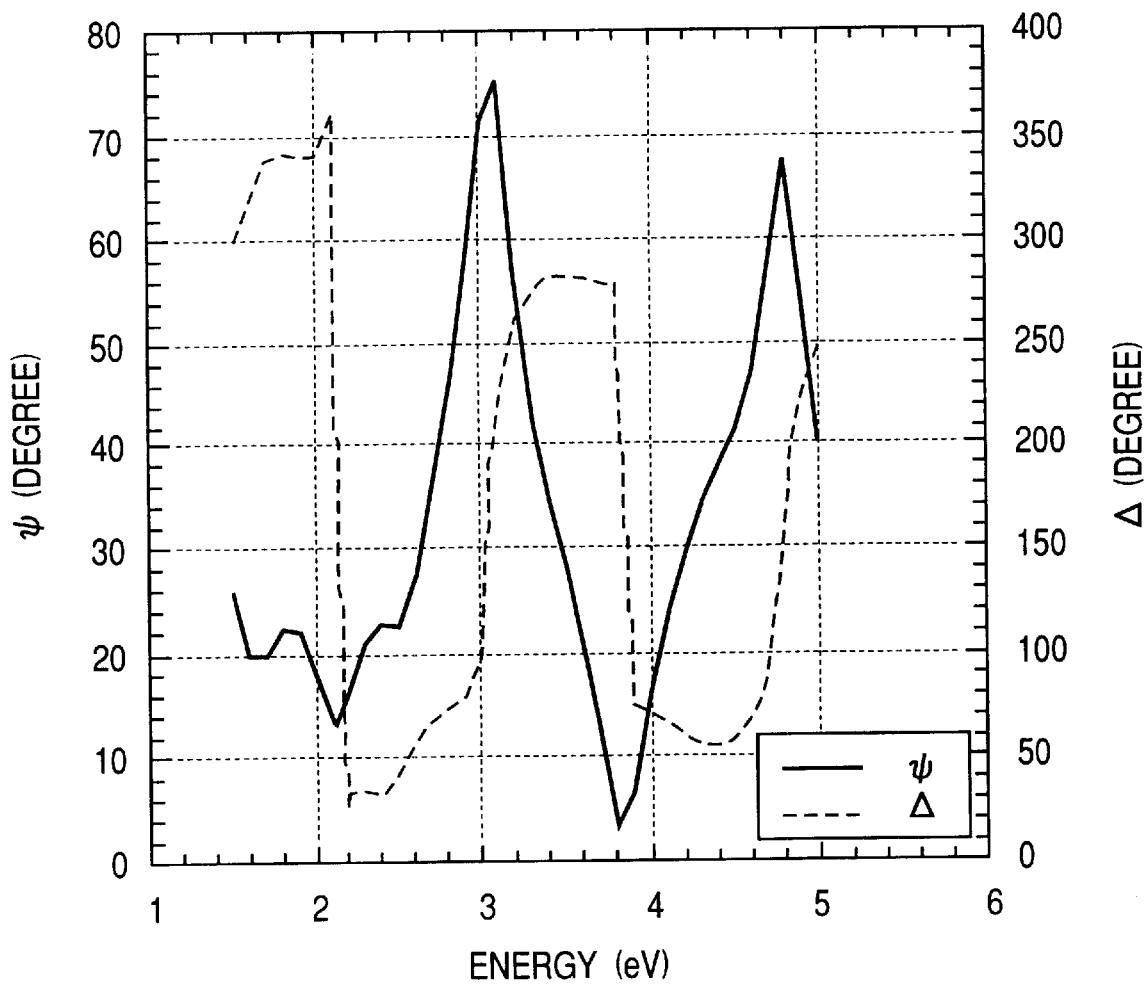
FIG. 7 shows a spectrum by a spectral ellipsometer after the selective epitaxial growth of SiGe shown in FIG. 6.

FIG. 6 shows a cross sectional view when a SiGe layer is selectively and epitaxially grown to 100 nm according to the pattern shown in FIG. 4. FIG. 7 shows the spectrum obtained by analyzing the sample with a spectral ellipsometer (the ordinates indicates the optical constants (ϕ, Δ) and the abscissa indicates the incident energy of incident light). The data includes one spectrum for the selectively grown SiGe layer of 100 nm with the spectra of the stacked film of $SiO_2$ and the polycrystalline silicon layer present in other area covered with the dielectric film, i.e., the spectra shown in FIG. 5.

Figure 8:
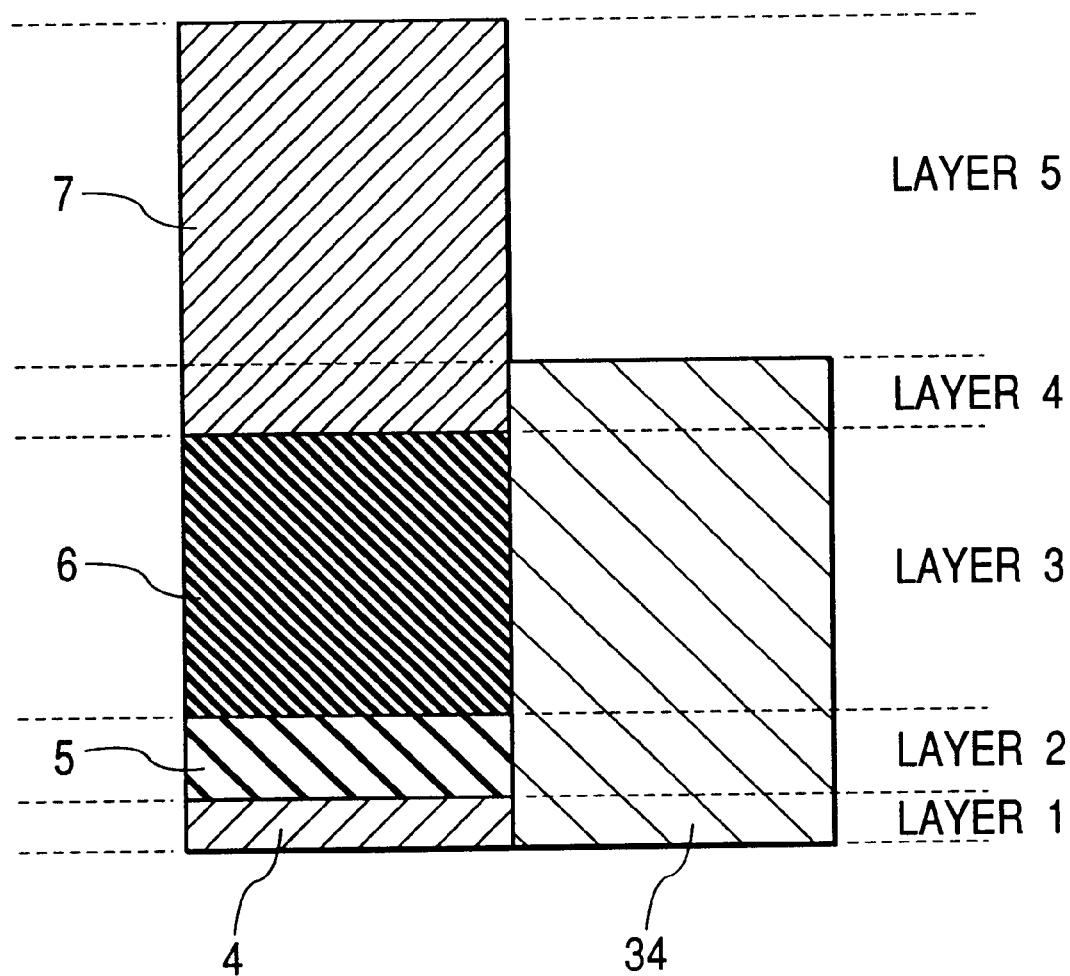
FIG. 8 is a cross sectional view of the semiconductor trench for explaining a method for analyzing the spectrum shown in FIG. 7 thereby determining the film thickness and the composition of SiGe.

FIG. 8 shows a method for analyzing the spectrum in FIG. 7 thereby determining the film thickness and the composition of SiGe. The layered structure as shown in FIG. 8 is separated into layers 1 to 5 as a model. The layer 1 contains a first dielectric film 4 and an SiGe film 34. The layer 2 contains a second dielectric film 5 and the SiGe film 34. The layer 3 contains a polycrystalline silicon layer 6 and the SiGe film 34. The layer 4 contains a third dielectric film 7 and the SiGe film 34. The layer 5 contains a third dielectric film 7 and air having a dielectric constant of 1.

In this case, each SiGe film thickness from layers 1 to 3 is fixed as the film thickness of the first dielectric film 4, the second dielectric film 4 and the polycrystalline silicon 6, respectively. Therefore, the film thickness and the composition of SiGe can be determined by fitting the resultant spectrum using the film thickness of the SiGe of the layer 4 and the SiGe composition from layers 1 to 4 as the parameter.

Figure 9:
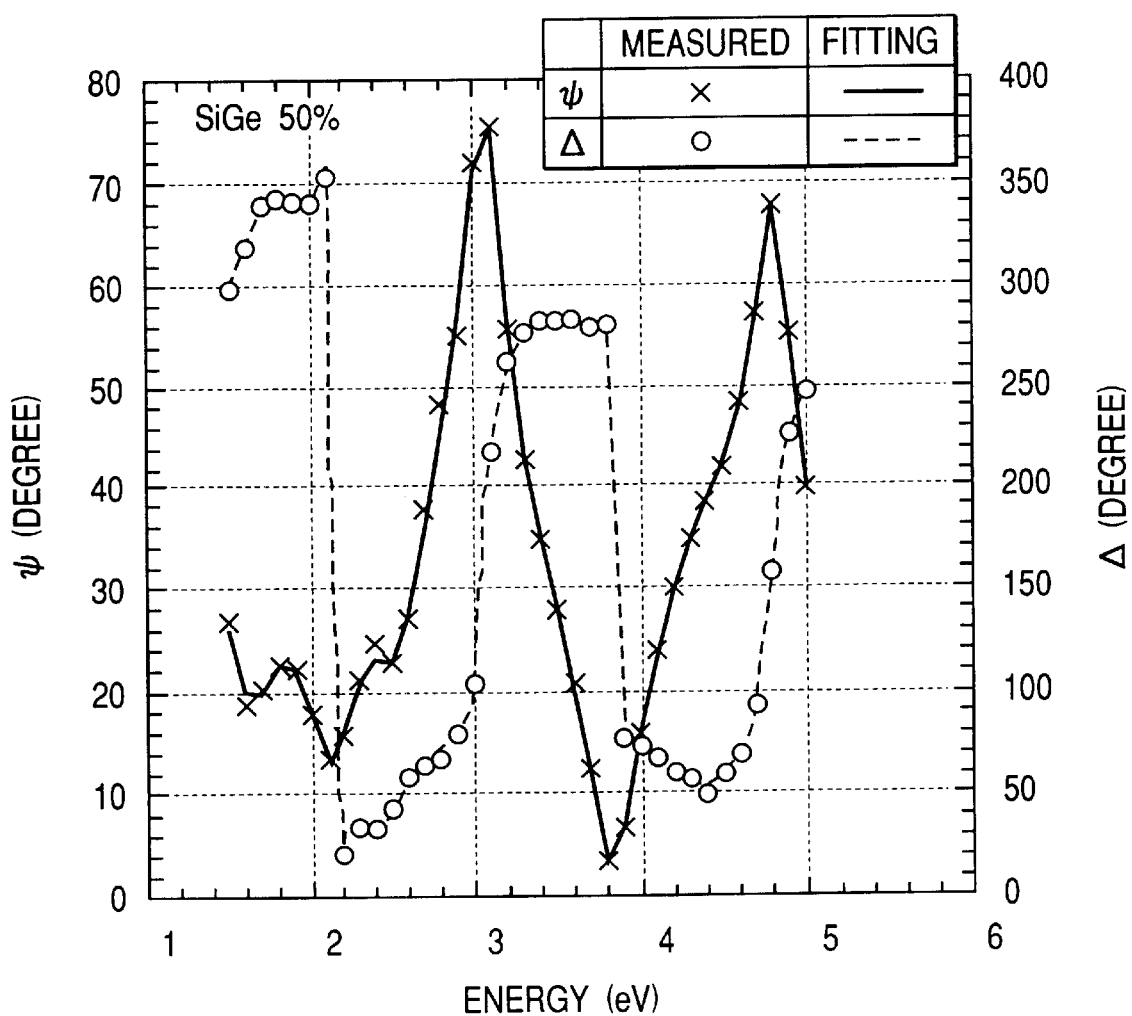
FIG. 9 is a graph for explaining the result of optical constant analysis in the third embodiment according to this invention.

FIG. 9 shows the result of the comparison. In this embodiment, the error relative to the measured value is minimized by fitting the spectrum with a sample obtained from a structure having a film with known thickness and composition. For example, the Ge concentration at 11.5% and the film thickness at 97 mm.

Figure 10:
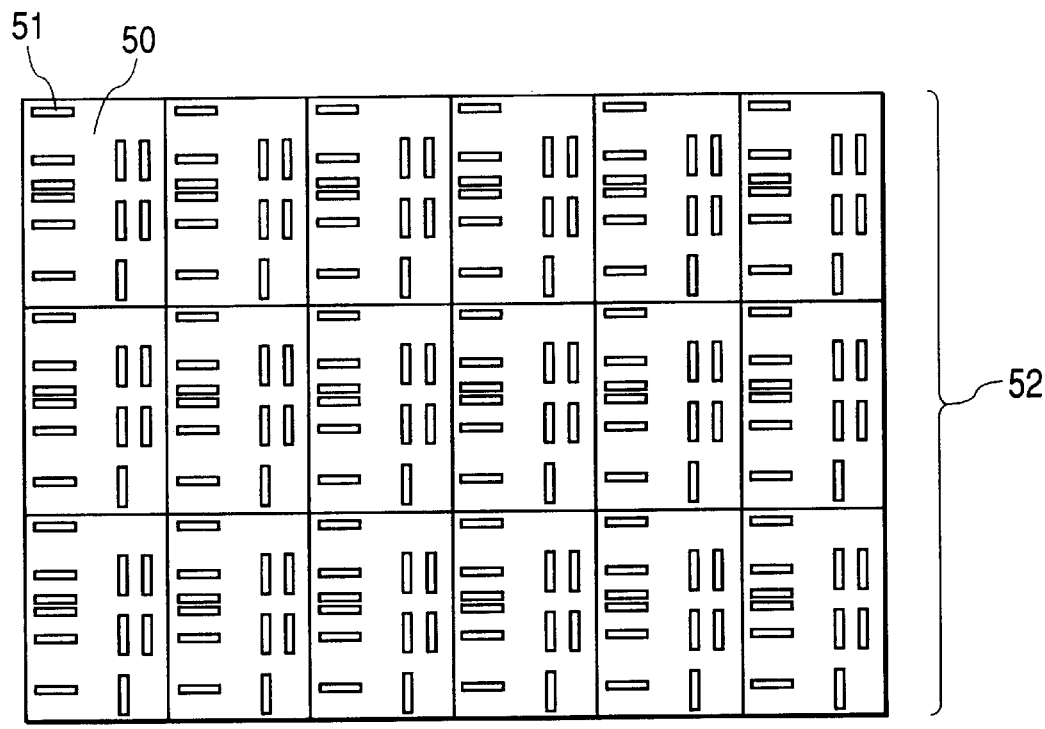
FIG. 10 shows a bipolar ECL gate array showing a fourth embodiment according to this invention.
Figure 11:
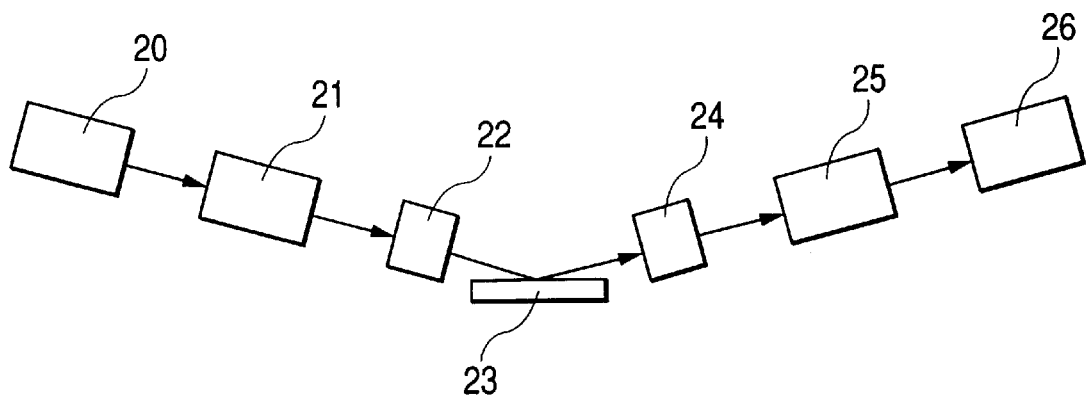
FIG. 11 is a principle view for spectral ellipsometry showing the prior art.
Figure 12:
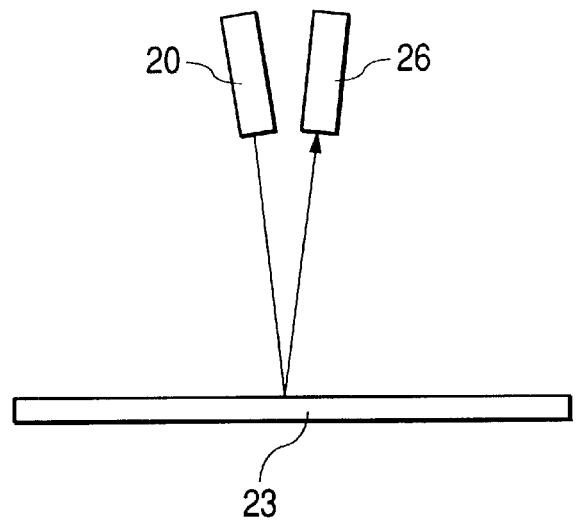
FIG. 12 is a principle view showing a reflectance method in the prior art.
Figure 13:
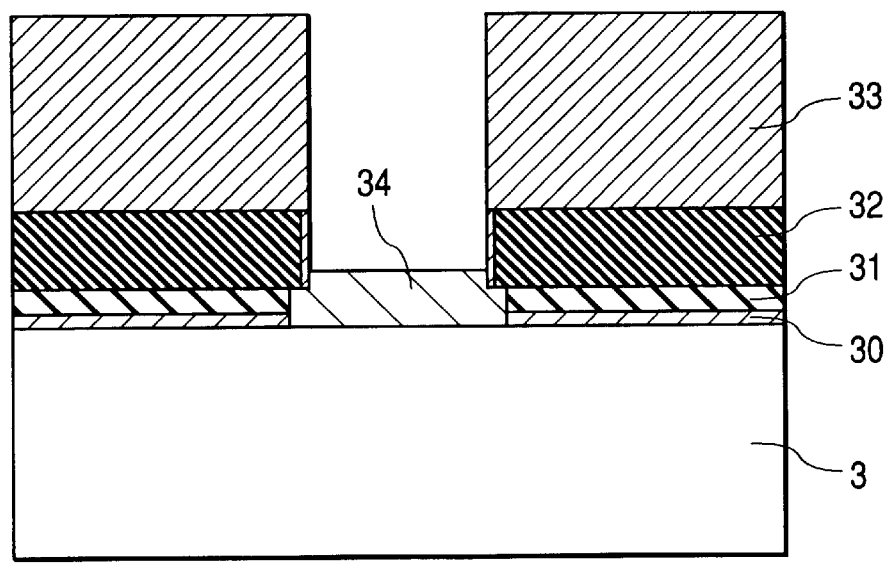
FIG. 13 is a cross sectional view of a SiGe hetero bipolar transistor.
Figure 14:
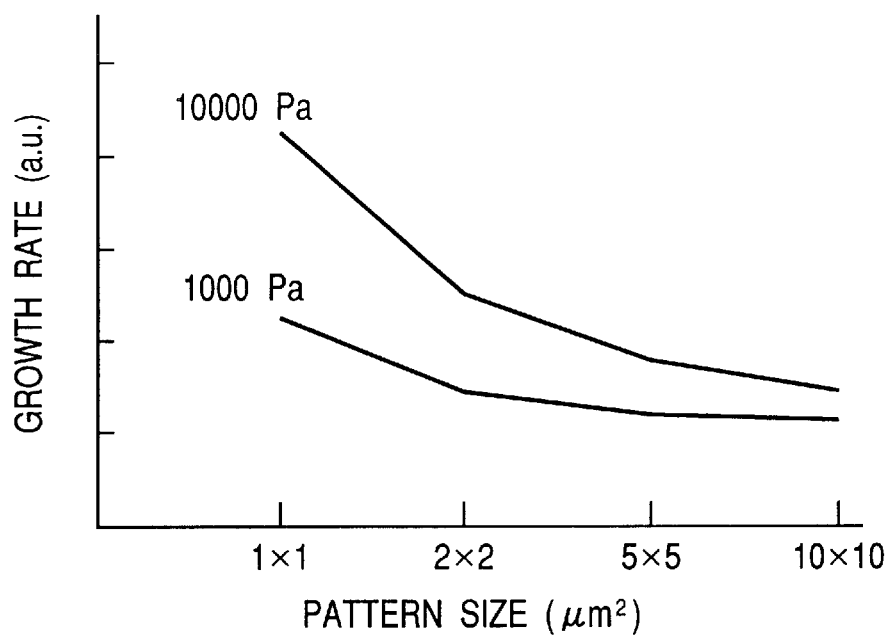
FIG. 14 is a graph explaining problems caused by the selective growth in the prior art.

FIG. 10 shows a bipolar ECL gate array as a fourth embodiment according to this invention. The drawing shows a plan view of an EC gate array pattern before forming an intrinsic base layer of a bipolar transistor. Plural windows 51 for the base selective epitaxial growth are arranged within the ECL gate area 50. The plural ECL gates 50 are arranged in parallel to form an ECL gate array 52.

The layout area of the ECL gate 50 illustrated here is 20 μm×40 μm, and the size of the gate array, for example, of 10000 gates is 2 mm×4 mm. The gate array is a pattern for manufacturing an actual LSI product. An incident light, from the ellipsometer is applied to the pattern to optically measure the thickness and the composition of the window 51 for base selective epitaxial growth, which can be fed back for manufacturing the next batch.

FIG. 15 to FIG. 18 show a fifth embodiment according to this invention.

Figure 15:
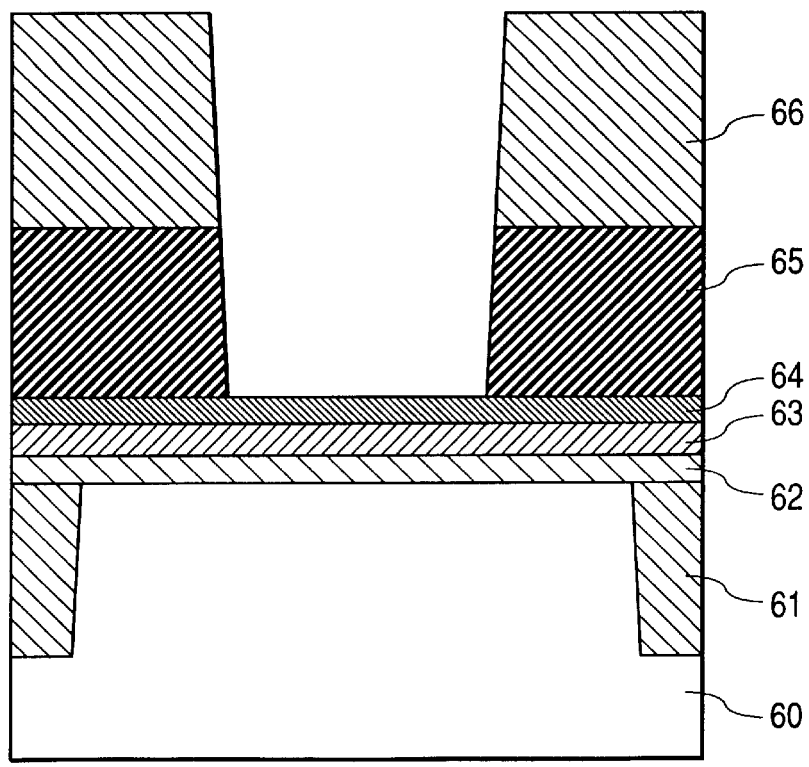
FIG. 15 is a cross sectional view showing the process (1) for making an SiGe hetero bipolar transistor in a fifth embodiment according to this invention.

In FIG. 15, a shallow trench isolation area 61 is formed onto a silicon substrate 60, and a multi-layered film comprising an $SiO_2$ film 62, a polysilicon film 63, a silicon nitride film 64, a boron doped polysilicon film 65 and an $SiO_2$ film 66 is also formed, then the $SiO_2$ film 66 and the boron doped polysilicon film 65 are partially removed by photolithography and dry etching. By the dry etching, a window as an intrinsic area of the bipolar transistor is formed.

Figure 16:
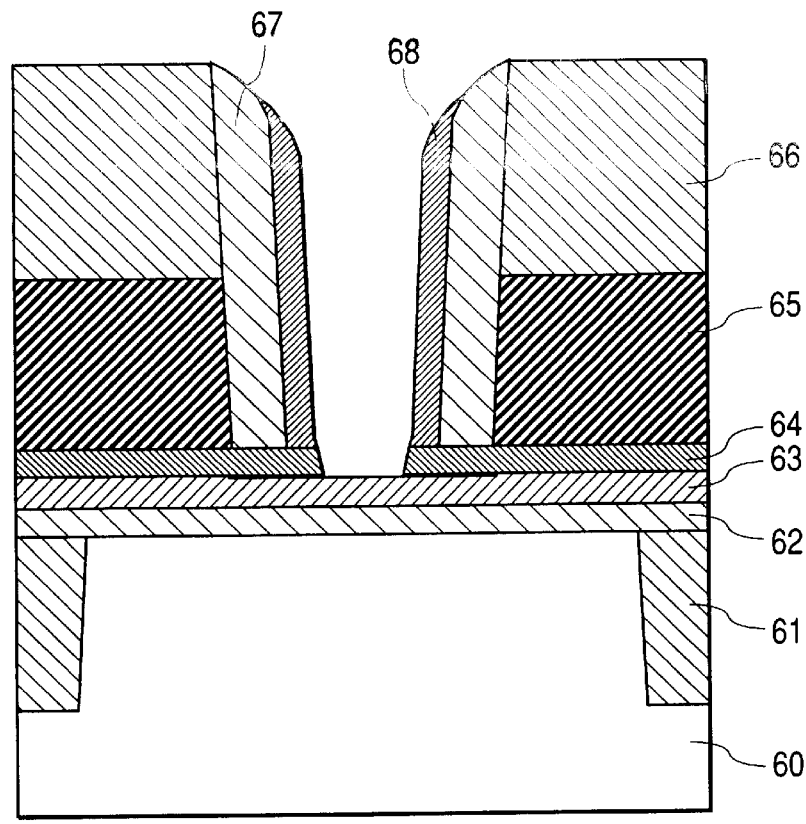
FIG. 16 is a cross sectional view showing the process (2) subsequent to FIG. 15.

Then, as shown in FIG. 16, an $SiO_2$ film 67 is deposited over the entire surface by CVD, a so-called side wall formation is conducted by dry etching. Then a silicon nitride film 68 is deposited over the entire surface, and the side wall formation is conducted again.

Figure 17:
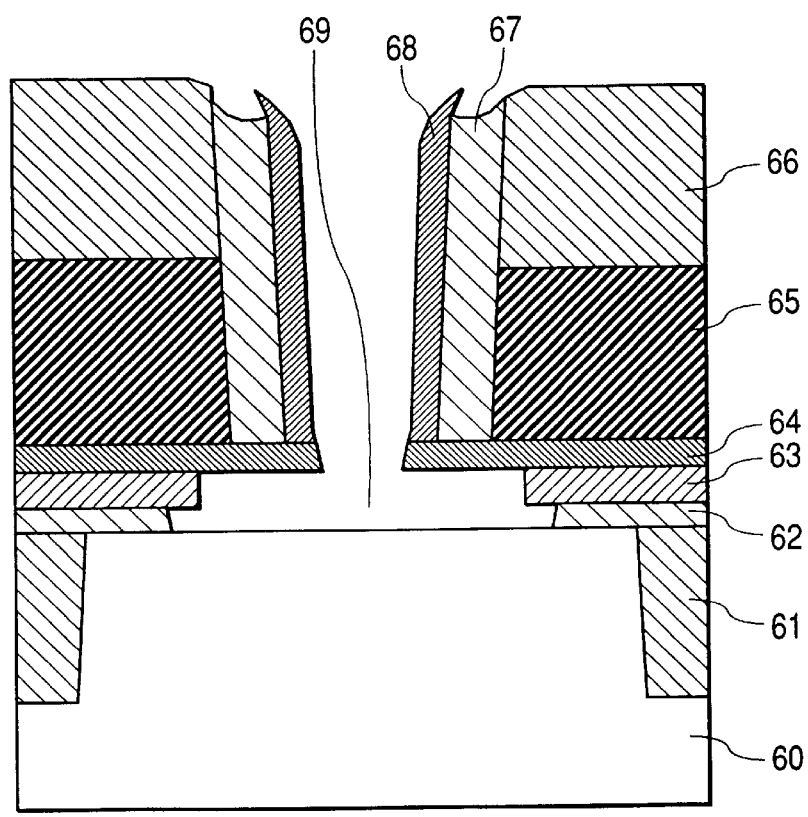
FIG. 17 is a cross sectional view showing the process (3) subsequent to FIG. 16.

Then as shown in FIG. 17, the polysilicon film 63 exposed to the window is etched by wet etching with hydrazine heated to 50° C., and etching is proceeded further laterally. Then, the $SiO_2$ film 62 is removed by wet etching with diluted hydrofluoric acid onto the surface of the silicon substrate 60. Then, the silicon nitride film 68 deposited on the side wall of the window is etched by phosphoric acid heated to 160° C. And the stacked silicon nitride film 64 is also etched laterally. An window 69 with the polysilicon overhang 65 is formed by the processing.

Figure 18:
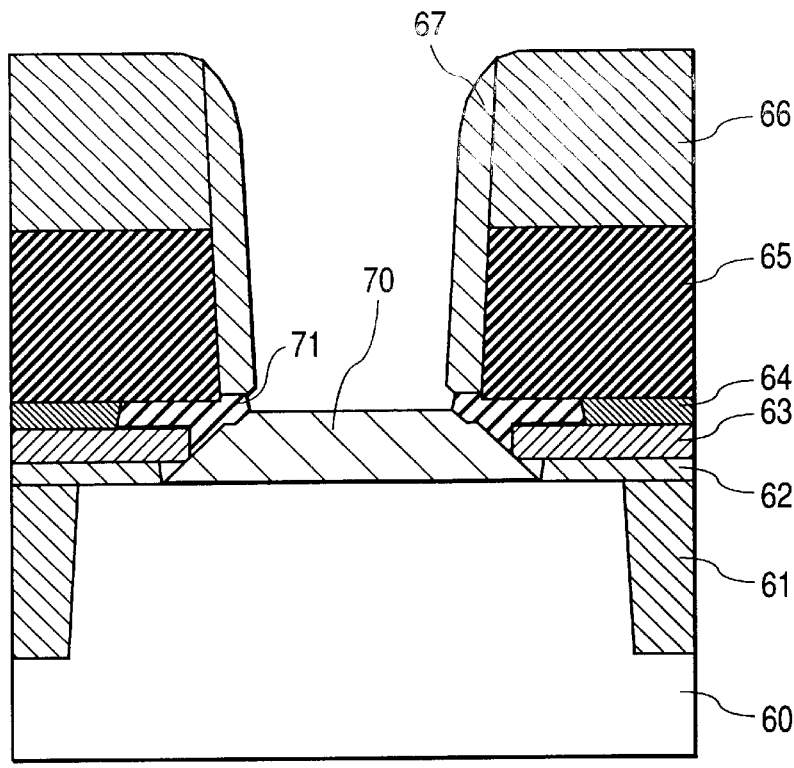
FIG. 18 is a cross sectional view showing the process (4) subsequent to FIG. 17.

As shown in FIG. 18, when the selectively and epitaxial SiGe grown is conducted by super high vacuum CVD using $Si_2H_6$, a $GeH_4$, $B_2H_6$ or the like, so-called selective growth is attained in which a single crystalline SiGe film 70 is formed at the bottom of the window where the silicon substrate 60 was exposed, a polycrystalline SiGe film 71 is formed below the overhang of the boron doped polysilicon film 65, and there is no film is grown on the $SiO_2$ film 66. The selectivity is improved further when growth is conducted in a halogen gas flow, such as $Cl_2$. Further, the gas may also be $SiH_4$, $SiH_2Cl_2$, $SiCl_4$ or $Ge_2H_6$, and the halogen gas may also be HCl or the like.

When the optical constants for the entire pattern are measured by a spectral ellipsometer after the selective growth, the spectrum as shown in FIG. 7 is obtained, and the film thickness and the composition of the selectively grown layer can be determined by analyzing the spectrum by the method shown in FIG. 8.

Figure 35:
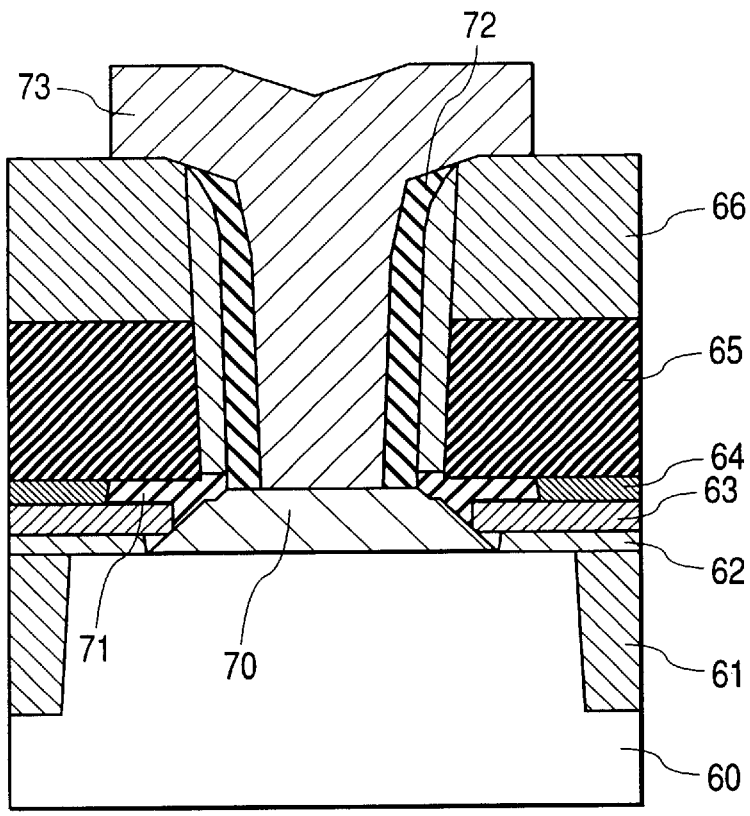
FIG. 35 is a cross sectional view of the hetero bipolar transistor formed by the processes shown in FIG. 15 to FIG. 18.

FIG. 35 shows a hetero bipolar transistor formed by the process depicted in FIG. 15 to FIG. 18. After forming the selectively grown single crystalline SiGe film 70, a side wall 72 comprising a silicon nitride film is formed by a so-called side wall forming process. Subsequently, a phosphorus-doped polysilicon film 73 is deposited to finish a bipolar transistor.

Figure 36:
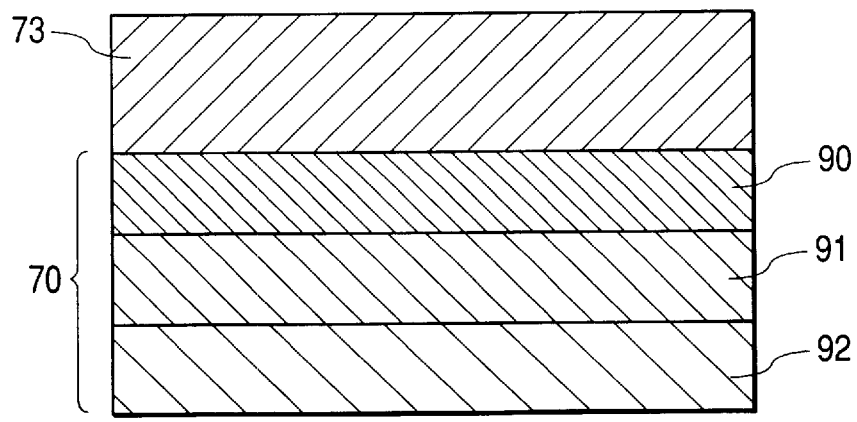
FIG. 36 is a cross sectional view of an intrinsic region of the hetero bipolar transistor shown in FIG. 35.

FIG. 36 shows an intrinsic region of the bipolar transistor shown in FIG. 35 in detail. The selectively grown single crystalline SiGe film 70 has a three-layered structure by stacking an N-single crystalline SiGe layer 92, a P-single crystalline SiGe layer 91 and an N-single crystalline Si layer 90 on the substrate.

The area for the N-single crystalline Si layer 90 is doped to the N-layer by thermal diffusion of phosphorus into the phosphorus doped polysilicon film 73. The P-single crystalline SiGe layer 91 is doped with, for example, a $B_2H_6$ gas during the selective growth. The N-single crystalline SiGe layer 92 may be doped with a $PH_3$ gas or the like during the selective growth. Alternatively, the doping can also be conducted by ion implantation. An NPN structure, of the bipolar transistor is formed. It is apparent that a PNP-transistor can also be formed by inverting making the conduction type for the respective layers.

Figure 19:
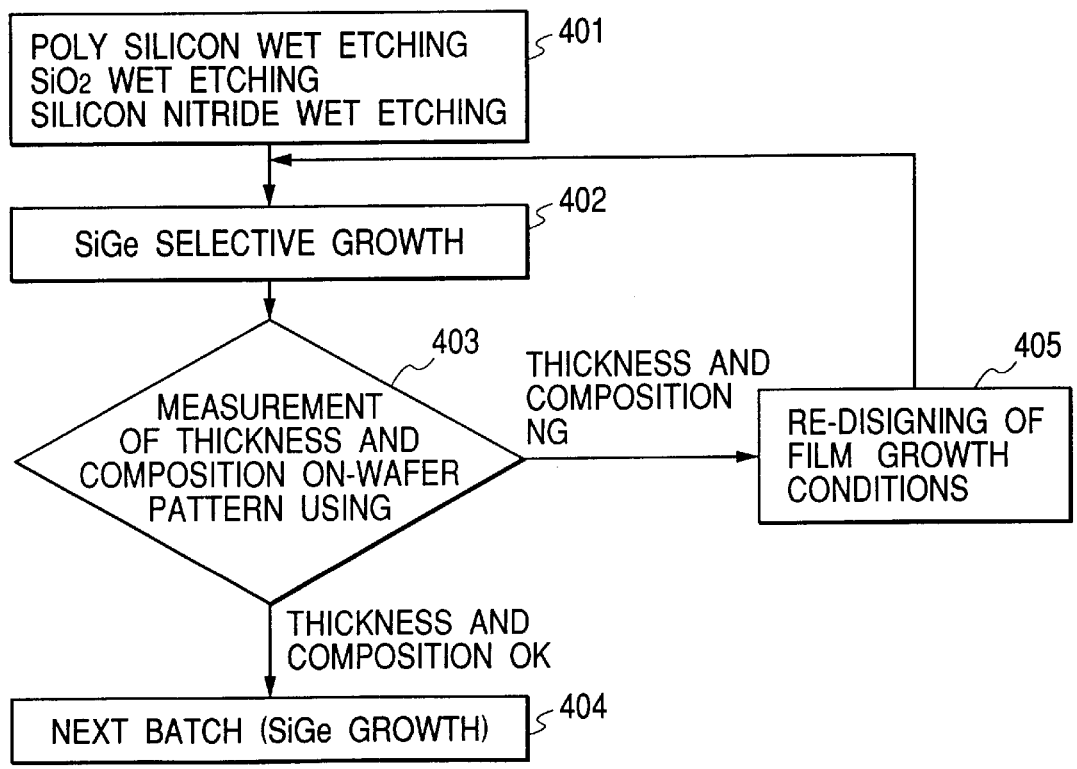
FIG. 19 is a flowchart of applying the invention to an SiGe hetero bipolar transistor as a sixth embodiment according to this invention.

FIG. 19 is a flowchart of the production method of a semiconductor device as a sixth embodiment according to this invention, which includes the processes described in FIG. 16 to FIG. 18. The polysilicon film 63 exposed in the window is etched by wet etching with hydrazine, then the $SiO_2$ film 62 is removed by wet etching with diluted hydrofluoric acid to expose some of the surface of the silicon substrate 60 (401). Then, the silicon nitride film 68 deposited on the side wall of the opening is etched with phosphoric acid, and the stacked silicon nitride film 64 is also etched laterally. A window 69 having an overhang of the boron-doped polysilicon film 65 is formed by the processing (401).

Then, a selectively and epitaxially grown SiGe layer is formed by so-called selective growth, in which the single crystalline SiGe film 70 is formed to a portion of the window where the silicon substrate 60 is exposed, the polycrystalline SiGe film 71 is formed below the overhang of the polysilicon film 65, and there is no film is grown on the $SiO_2$ film 66 (402). Subsequently, the composition and the film thickness of the selectively grown SiGe layer are measured by an on-wafer pattern (403). When the measuring result matches with the designed composition and the film thickness (OK), the processing for the next batch (SiGe growth) is conducted under the same conditions (404) and, if the composition and the film thickness are different from the design (NG), the growth conditions for the next batch are redesigned (405). By the process control as described above, failure caused by the selective growth can be prevented from continuing thereby improving the yield.

Figure 20:
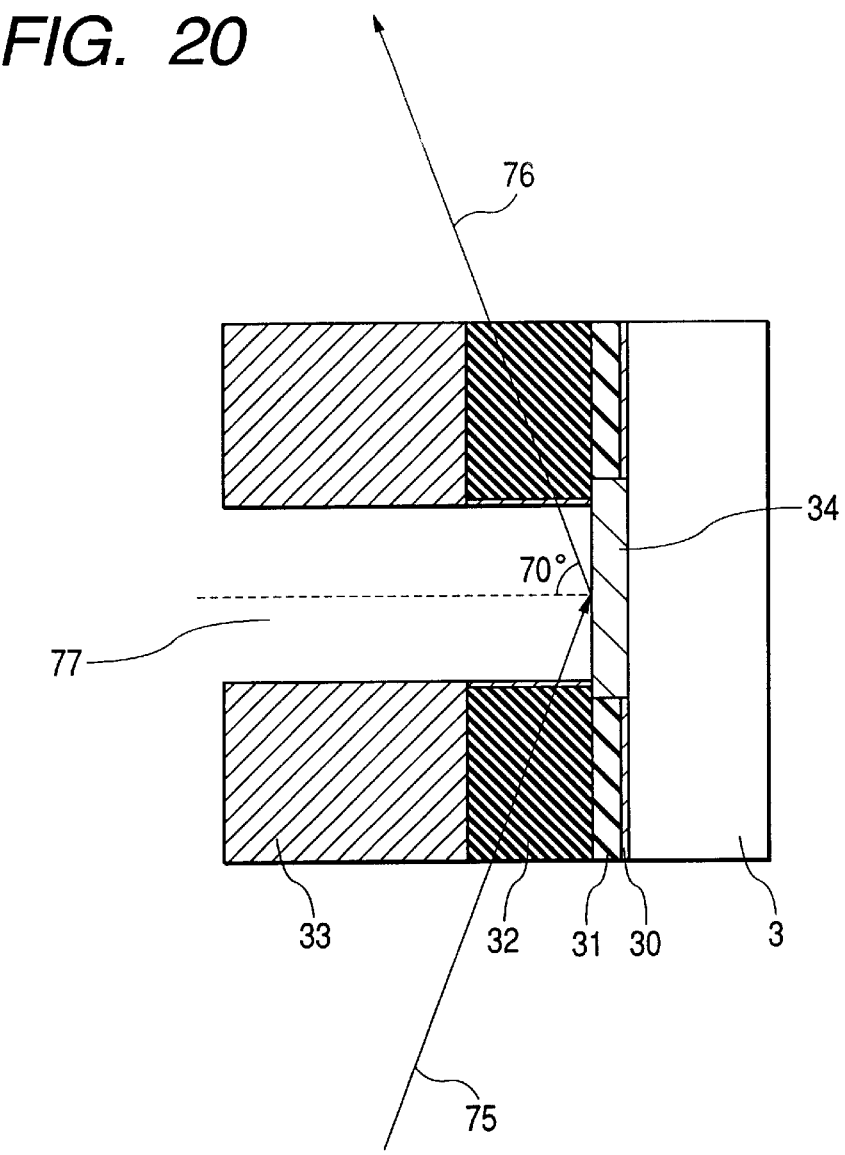
FIG. 20 shows how to measure a selectively grown layer (1) in a seventh embodiment according to this invention.

FIG. 20 shows a seventh embodiment according to this invention. This is a view when an incident light 75 of an ellipsometer is entered at an angle of 70° to a measurement pattern formed by stacking a film comprising a first silicon oxide film 30, a silicon nitride film 31, a polysilicon film 32 for extrinsic base and a second silicon oxide film 33, and forming an selectively and epitaxially grown SiGe layer 34 to the window. 76 in the drawing represents a reflected light.

The thickness for each of the stacked films is 10 nm for the first silicon oxide film 30, 50 nm for the silicon nitride film 31, 200 nm for the polysilicon film 32 for extrinsic base, 400 nm for the second silicon oxide film 33 and 70 nm for the selectively and epitaxially grown SiGe layer 34. The width for the window is, for example, 0.3 $\mu$m.

As apparent from FIG. 20, the incident light 75 does not enter directly at an incident angle of 70° to the selectively and epitaxially grown layer 34 but enters by way of the polycrystalline silicon film 32 for extrinsic base, the silicon oxide film 33, or the window 77. Also in this case, the accurate film thickness or composition can be determined by analyzing on every layers as shown in FIG. 8.

Figure 21:
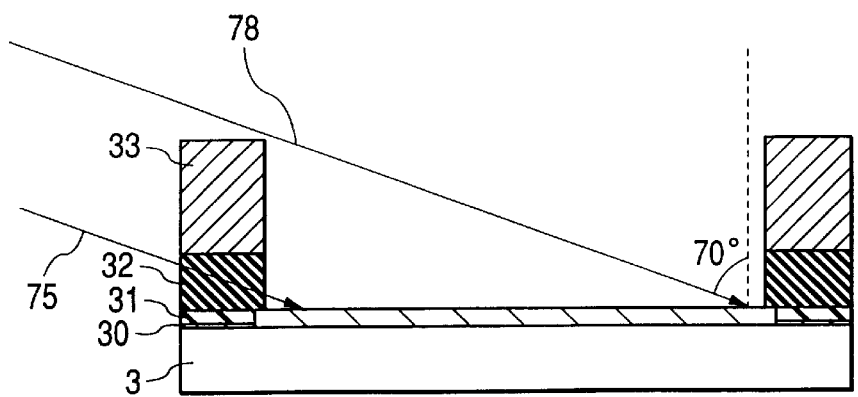
FIG. 21 shows how to measure a selectively grown layer (2) in the seventh embodiment according to this invention.

FIG. 21 shows a seventh embodiment according to this invention. An incident light enters at an angle of 70° from an ellipsometer in parallel with a slitwise measurement pattern. The size of the slit is, for example, 0.2 $\mu$m×2 $\mu$m. In this case, an incident light 78 entering directly to the selectively and epitaxially grown layer 34 is present. Also in this case, the film thickness and the composition can be determined by the method shown in FIG. 8.

Figure 22:
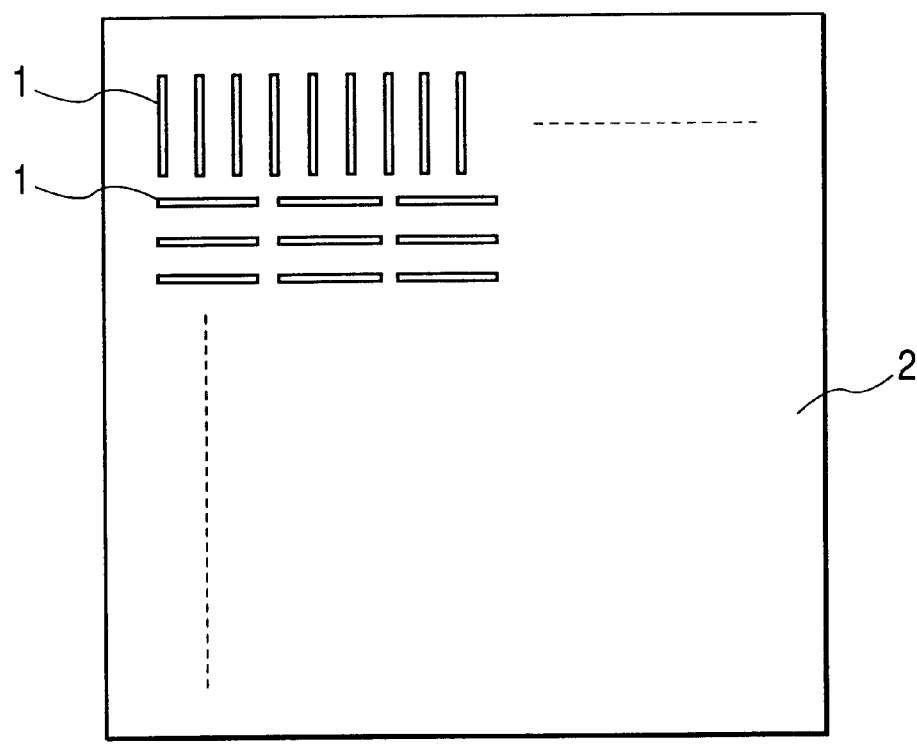
FIG. 22 is a view of a measurement pattern in an eighth embodiment according to this invention.

FIG. 22 shows an eighth embodiment according to this invention. The drawing shows a method for reducing an error along with the path of the incident light as shown in FIG. 20 and FIG. 21. By alternating the direction of the patterns for different rows in the selective growth area 1 by 90°, the error along the path of the incident light can be reduced such that accuracy is further improved. In this case, similar effect can be obtained also by arranging the angle of the growth pattern at random.

In particular, if the incident beam enters as shown in FIG. 20, no light beam directly enters the selective growth layer at the bottom of the trench, which degrades the accuracy of the measurement. On the other hand, by having a second group of trenches shown in FIG. 21 lain perpendicular to the first group of trenches as shown in FIG. 20, the second group of trenches will all received the same incident light beam direct at the bottom of the trenches as shown in FIG. 21. As such, the degrading effect of the first group of trenches is 50% evened out by the second group of trenches. By analogy, a random pattern of trenches of various orientations can further reduce the degrading effect regardless of the orientation of the trenches with respect to the direction of the incident light beam.

Figure 23:
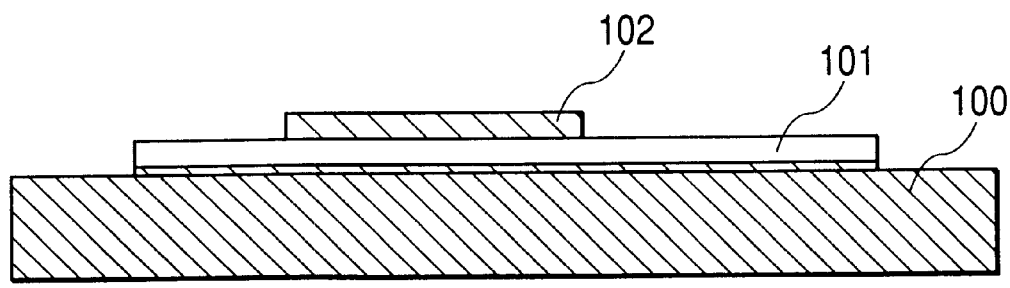
FIG. 23 is a cross sectional view for explaining a process (1) for making a polysilicon resistor in a ninth embodiment according to this invention.

FIG. 23 shows a ninth embodiment according to this invention, which is a process for forming a polysilicon resistor. A resistor element 101 comprising polysilicon is patterned on a dielectric film 100 and, further, a silicon oxide film 104 formed on the resistor element 101 is patterned.

Figure 24:
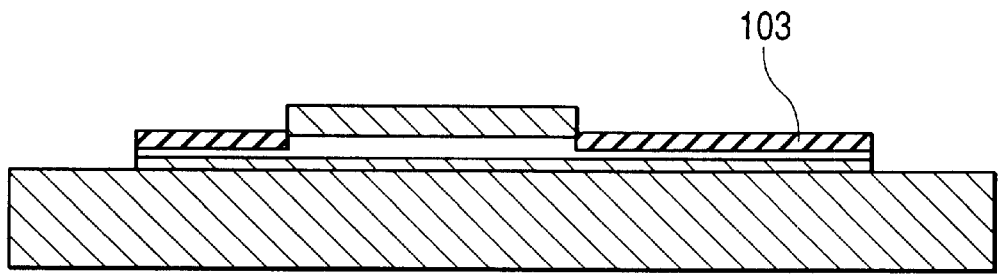
FIG. 24 is a cross sectional view for explaining a process (2) subsequent to FIG. 23.

Then, as shown in FIG. 24, a metal film, such as titanium, is formed, and annealing is conducted to form a metal silicide film 103, such as $TiSi_2$, selectively, only on the surface where the polysilicon is exposed.

Figure 25:
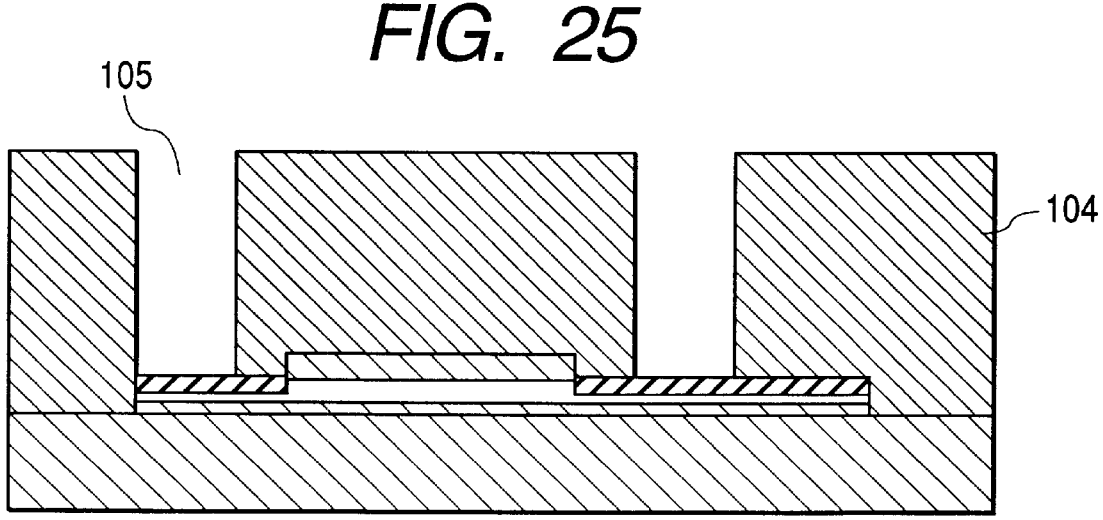
FIG. 25 is a cross sectional view for explaining a process (3) subsequent to FIG. 24.

Then, as shown in FIG. 25, an interlayer dielectric film 104 is formed, and only the portion forming the electrode is removed by dry etching to expose a contact opening 105.

Figure 26:
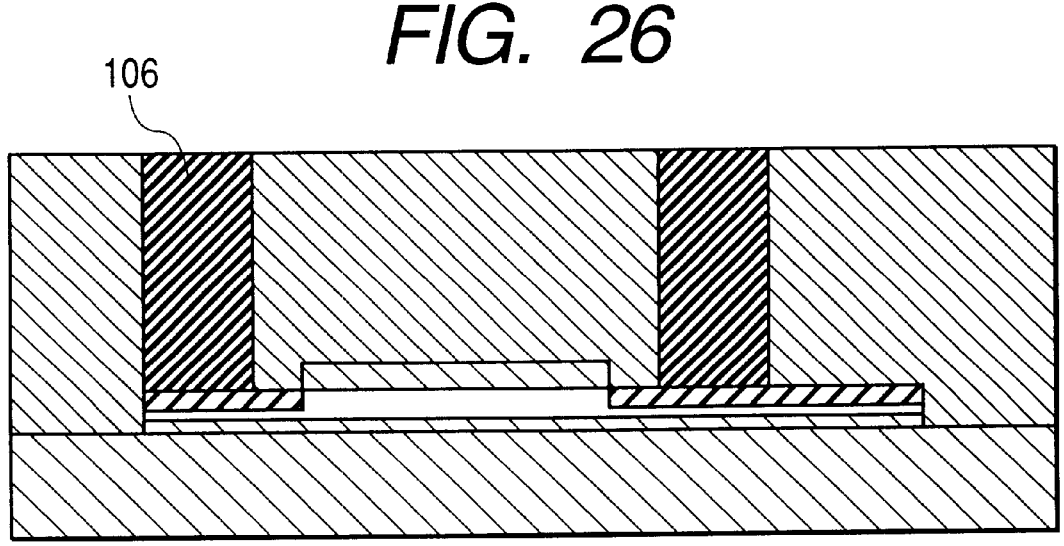
FIG. 26 is a cross sectional view for explaining a process (4) subsequent to FIG. 25.

When, as shown in FIG. 26, a tungsten electrode 106 is formed, for example, by a selective growing method using, for example, a $WF_6$ gas and $SiH_2F_2$. In this case, the tungsten electrode 106 may be formed by planarizing (chemical mechanical polishing) after tungsten is grown over the entire surface. Also for such a structure, the film thickness of the buried tungsten electrode can be determined by optical constants for the entire pattern and analyzed by the method shown in FIG. 8.

In this embodiment, the tungsten electrode formed in a polysilicon resistor is mentioned as an example, but it may be a transistor or a diode, as well as a capacitor or an inductor. Further, the electrode material is not limited to a metal, such as tungsten or aluminum, but also may be a polysilicon with an impurity at high concentration.

FIG. 27 to FIG. 33 show a tenth embodiment according to this invention, which is processing for a hetero bipolar transistor using the non-selective (i.e., blanket) simultaneous growth of single crystal SiGe and polycrystal SiGe.

Figure 27:
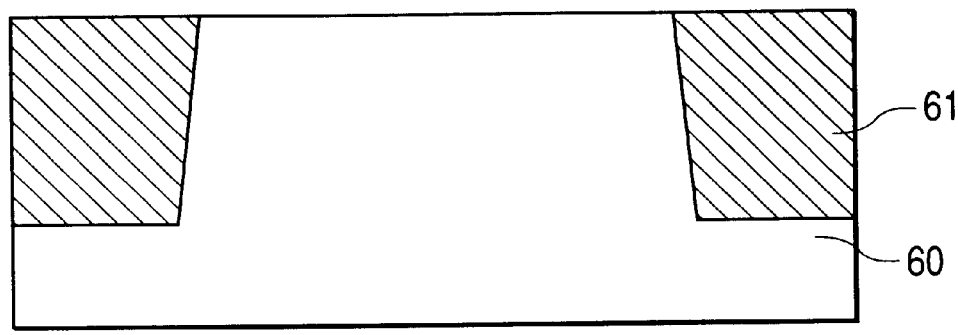
FIG. 27 is a cross sectional view for explaining a process (1) for making an SiGe hetero bipolar transistor using non-selective growth in a tenth embodiment according to this invention.

At first, as shown in FIG. 27, a device isolation oxide film 61 is formed to a silicon substrate 60. It is apparent that sub-collector and collector areas have already been formed.

Figure 28:
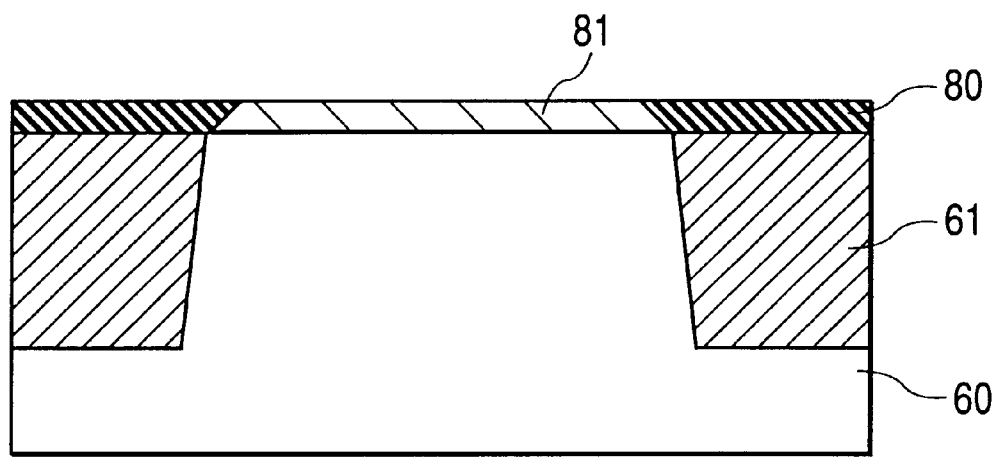
FIG. 28 is a cross sectional view for explaining a process (2) subsequent to FIG. 27.

Then as shown in FIG. 28, a single crystalline SiGe film 81 is grown on the silicon substrate 60, and a polycrystalline SiGe film 80 is grown simultaneously on the device isolation oxide film 61 by a method, such as CVD or MBE. The simultaneous growth for single crystals and polycrystals is conducted by a solid source MBE or CVD in a case of using only a hydrogenated gas, such as $SiH_4$ or $GeH_4$.

Figure 29:
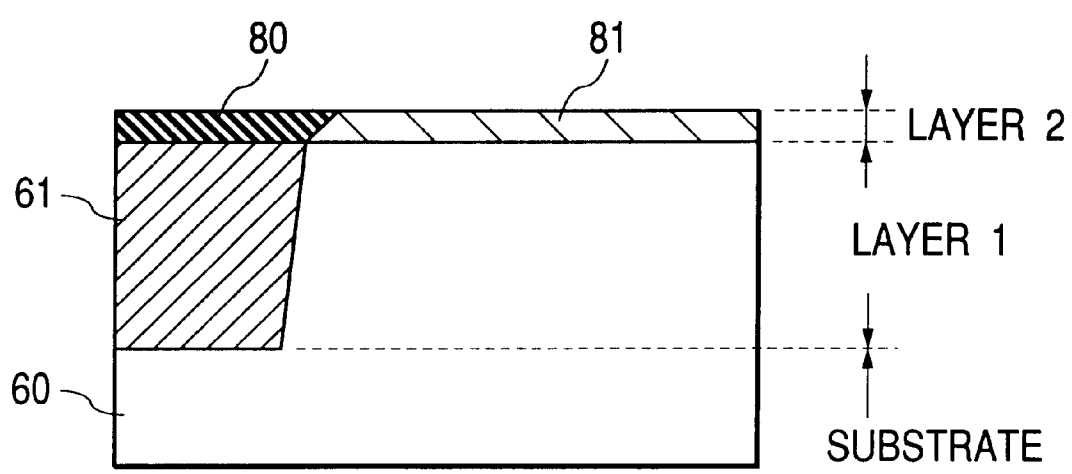
FIG. 29 is a cross sectional view for explaining a process (3) subsequent to FIG. 28.

After the single crystals and the polycrystals are simultaneously grown, optical constants of a pattern for closely arranged transistors, such as a measurement pattern or gate array, formed simultaneously on-wafer are measured, for example, by ellipsometry. By analyzing the result on each of the layers as shown in FIG. 29, the composition and the film thickness of the single crystalline SiGe film 81 and the polycrystalline SiGe film 80 are determined. That is, analysis may be conducted for the layer 1 containing the device isolation oxide film 61 and the substrate 60, and for the layer 2 containing the polycrystalline SiGe film 80 and the single crystalline SiGe film 81.

Figure 30:
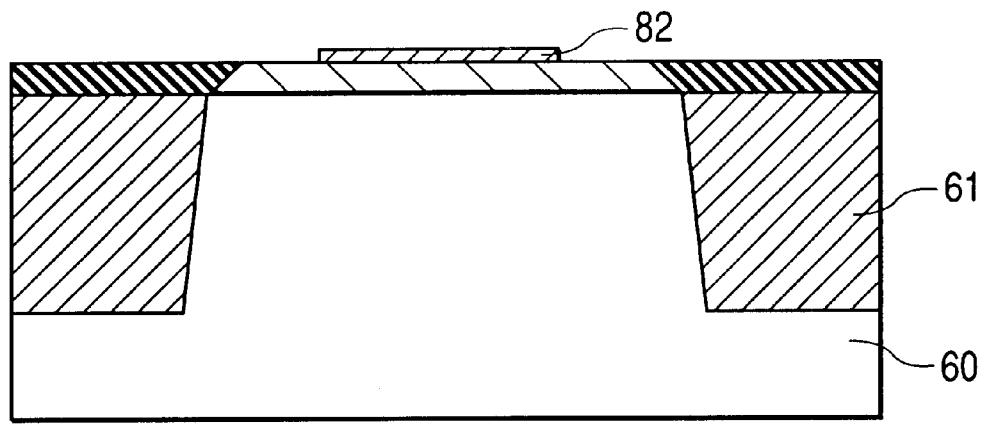
FIG. 30 is a cross sectional view for explaining a process (4) subsequent to FIG. 29.

After determining the composition and the film thickness of the SiGe film by this method, the pad oxide film 82 is deposited on the single crystalline SiGe as shown in FIG. 30. The thickness of the pad oxide film is, for example, about 10 nm.

Figure 31:
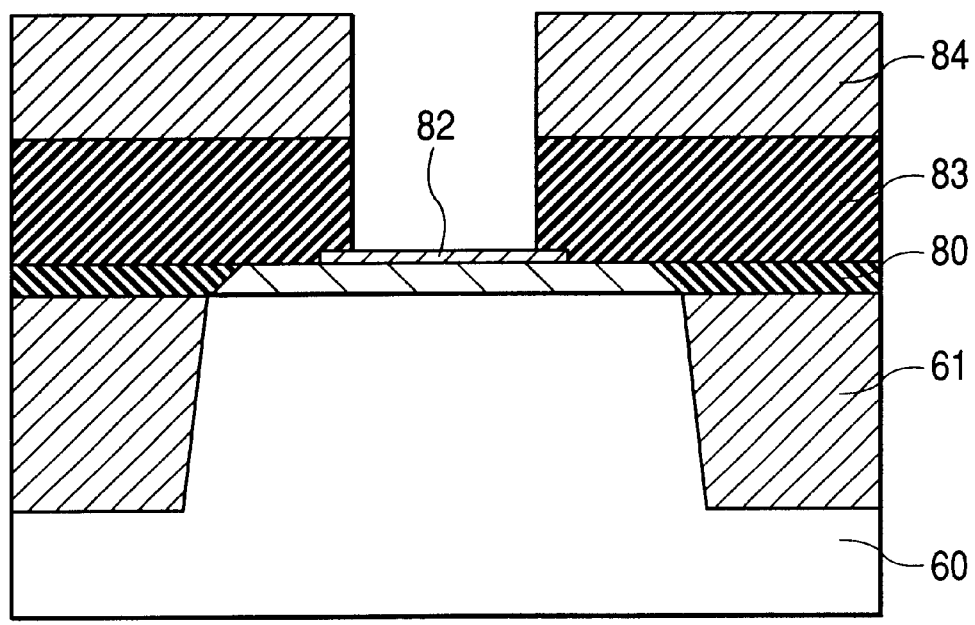
FIG. 31 is a cross sectional view for explaining a process (5) subsequent to FIG. 30.

As shown in FIG. 31, after stacking a base polysilicon film 83 and the silicon oxide film 84, the pad oxide film 82 is exposed partially by photolithography and dry etching. Thus, the emitter area of the bipolar transistor is formed.

Figure 32:
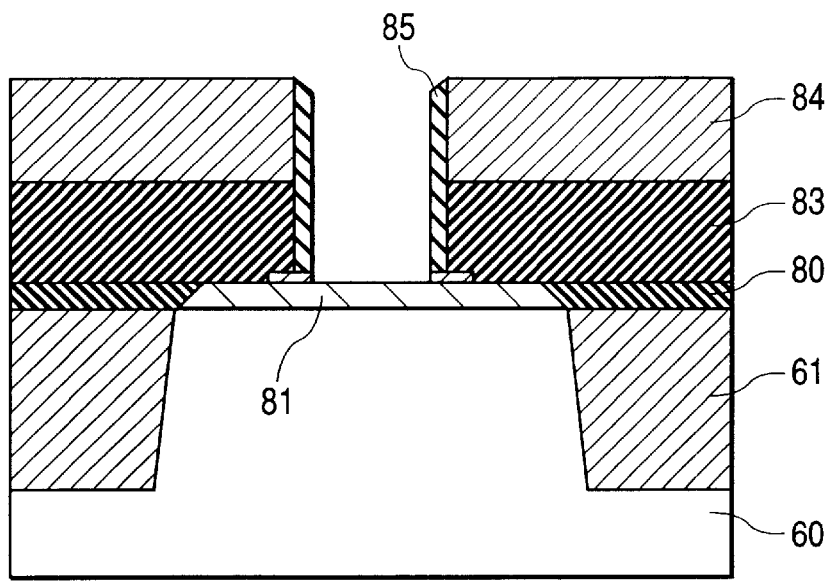
FIG. 32 is a cross sectional view for explaining a process (6) subsequent to FIG. 31.

Then as shown in FIG. 32, a side wall comprising a silicon nitride film 85 is formed in the emitter area by the side wall leaving process, and the pad oxide film 82 in the emitter area is removed by wet etching with hydrofluoric acid to expose the single crystalline SiGe film 81.

Figure 33:
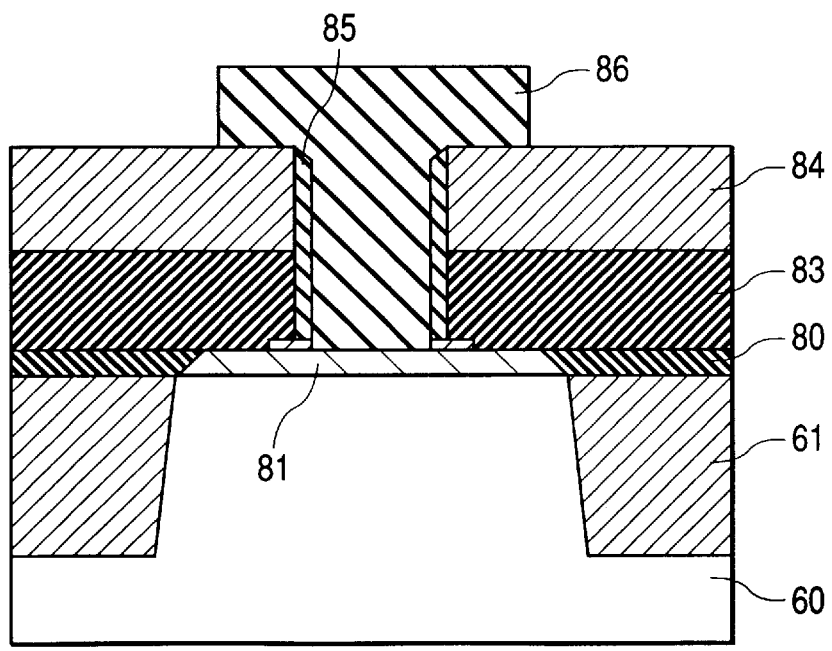
FIG. 33 is a cross sectional view for explaining a process (7) subsequent to FIG. 32.

Then, by forming a phosphorus-doped emitter polysilicon film 86 on a single crystalline SiGe film 81 and patterning the same, an intrinsic region of the bipolar transistor is formed as shown in FIG. 33. The film quality controlling method according to this invention is effective also for the process using non-selective growth over the entire surface.

Figure 34:
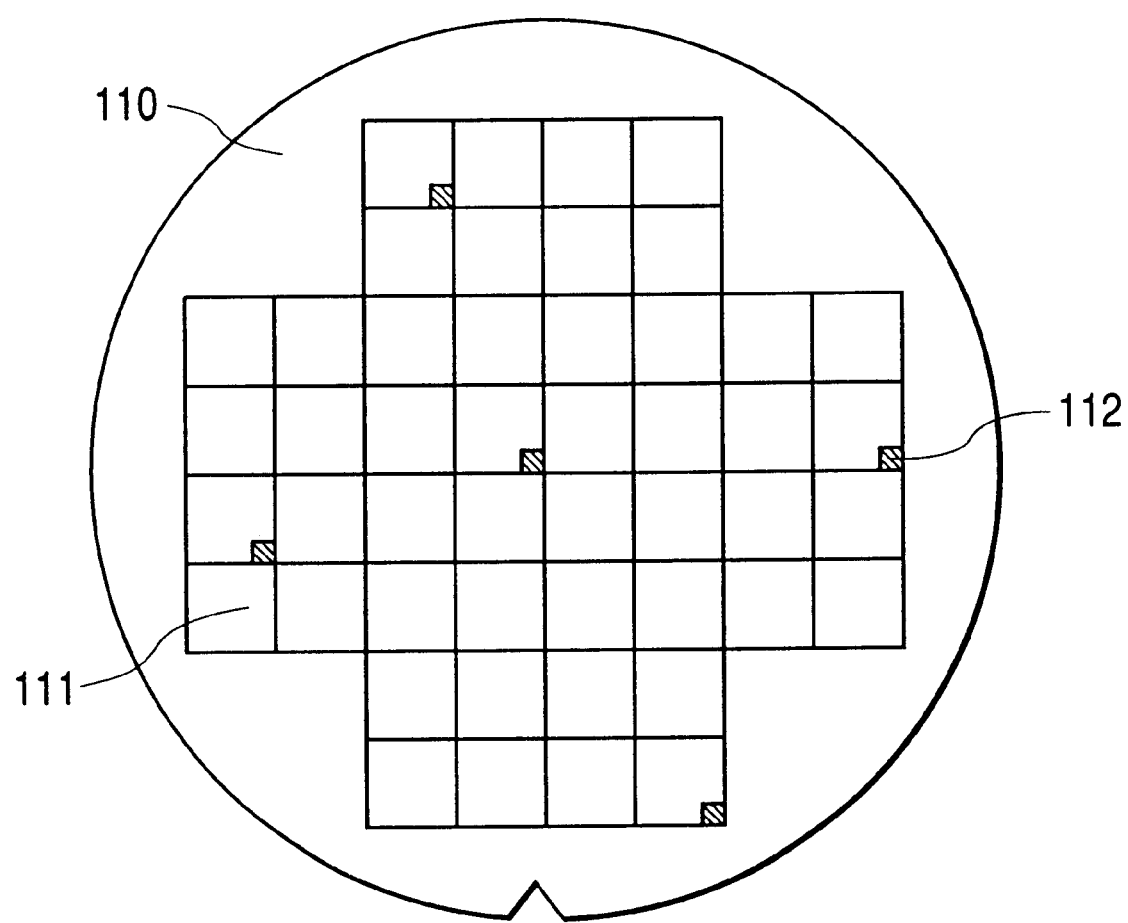
FIG. 34 shows an arrangement of an on-wafer measurement pattern in an eleventh embodiment according to this invention.

FIG. 34 shows an eleventh embodiment according to this invention which an arrangement of an on-wafer measurement pattern on the semiconductor wafer. Usually, integrated circuit patterns 11 are disposed in plurality as shown in the drawing on the semiconductor wafer 110. Plural on-wafer measurement patterns 112 are arranged therein and optical constants for each of them are measured, by which thickness variation throughout a wafer, for example, for the thickness of the thus formed thin films can be measured just after the formation of the thin film. When information regarding the thickness variation throughout a wafer is fed back to the next batch to reduce the thickness variation throughout a wafer, yield of the integrated circuits can be improved.

In the embodiments described above, discussion has been focused on an example of using the ellipsometry for measuring the thickness of the thin film but this invention is not restricted to such a method. A reflectance method is also applicable. Further, the semiconductor to be applied according to the invention may also be mixed crystals containing silicon, germanium and carbon instead of the mixed crystals containing silicon and germanium.

As has been described above, this invention provides a non-destructive inspection method of a selectively grown film and a manufacturing method of a semiconductor device with a simple and convenient process control and improved throughput.

Further, since the thickness and the composition of the thin film grown on the fine pattern can be monitored in the production line, the yield of LSI is improved.

The foregoing invention has been described in terms of preferred embodiments. However, those skilled in the art will recognize that many variations of such embodiments exist. Such variations are intended to be within the scope of the present invention and the appended claims.

What is claimed is:

1. A method for manufacturing a semiconductor device on a semiconductor wafer, comprising:

forming a dielectric film on a surface of a semiconductor substrate;

forming a window in the dielectric film through which a portion of the surface of the semiconductor substrate is exposed;

growing a semiconductor in the window;

determining at least one of thickness and composition of a thin film, which is grown within at least one trench formed by etching through plural substances exposed on the wafer by using a measurement pattern formed on the wafer, by comparing at least one physics characteristic of the wafer before and after the film is formed; and adjusting at least one growth condition for making the thin film of next batch based upon the comparing result.

2. The method for manufacturing a semiconductor device according to claim 1, wherein the semiconductor comprises silicon and mixed crystals containing silicon and germanium.

3. The method for manufacturing a semiconductor device according to claim 1, wherein the semiconductor comprises silicon and mixed crystals containing silicon, germanium and carbon.

* * * * *